United States Patent

Shain et al.

[11] Patent Number: 6,027,459
[45] Date of Patent: Feb. 22, 2000

[54] METHOD AND APPARATUS FOR OBTAINING BLOOD FOR DIAGNOSTIC TESTS

[75] Inventors: Eric B. Shain, Glencoe; Michael G. Lowery, Wildwood; David D. Cunningham, Lake Villa; Timothy P. Henning, Vernon Hills; Douglas F. Young, Grayslake, all of Ill.

[73] Assignee: Abbott Laboratories, Abbott Park, Ill.

[21] Appl. No.: 08/982,561

[22] Filed: Dec. 2, 1997

Related U.S. Application Data

[63] Continuation-in-part of application No. 08/759,698, Dec. 6, 1996.
[60] Provisional application No. 60/036,395, Jan. 24, 1997.

[51] Int. Cl.⁷ .................................................. A61B 10/00
[52] U.S. Cl. ........................................... 600/573; 606/181
[58] Field of Search .................................. 600/573, 578, 600/583, 584; 606/181, 182

[56] References Cited

U.S. PATENT DOCUMENTS

| | | |
|---|---|---|
| Re. 32,922 | 5/1989 | Levin et al. . |
| 3,933,439 | 1/1976 | McDonald . |
| 4,203,446 | 5/1980 | Hofert et al. . |
| 4,375,815 | 3/1983 | Burns . |
| 4,539,988 | 9/1985 | Shirley et al. . |

(List continued on next page.)

FOREIGN PATENT DOCUMENTS

| | | |
|---|---|---|
| 0021798 | 1/1981 | European Pat. Off. . |
| 0212906 | 3/1987 | European Pat. Off. . |
| 0230472 | 8/1987 | European Pat. Off. . |
| 0254203 | 1/1988 | European Pat. Off. . |
| 0371503 | 6/1990 | European Pat. Off. . |

(List continued on next page.)

OTHER PUBLICATIONS

R.J. Lane et al., "Ultraviolet–Laser Ablation of Skin", IBM Research Report, (1984).

*Primary Examiner*—Cary O'Connor
*Assistant Examiner*—Pamela L. Wingood
*Attorney, Agent, or Firm*—David L. Weinstein

[57] ABSTRACT

Method and apparatus for obtaining a sample of blood from a patient for subsequent diagnostic tests, e.g., glucose monitoring. In one aspect of the invention, the method comprises the steps of:

(a) forming an unobstructed opening in the area of the skin from which the sample of blood is to be extracted; and (b) extracting the sample of blood from the unobstructed opening in the skin, with the aid of a vacuum and a stretching of the skin.

In another aspect of the invention, an apparatus for carrying out the method described previously is provided. The apparatus comprises:

(a) a device for forming an unobstructed opening in an area of skin from which said sample is to be extracted, preferably a lancing assembly; and (b) a vacuum pump.

Preferably, the apparatus also includes a housing.

In a further aspect of the invention, a pneumatic lancing assembly is provided. The pneumatic lancing assembly uses differential gas pressure to thrust a lancet into skin tissue. This lancing assembly effectively utilizes low-pressure gas, which is preferably provided by the aforementioned vacuum pump, and high-pressure gas, which is preferably provided by ambient air surrounding the apparatus, to thrust the lancet, puncture the skin, and then retract the lancet from the skin to produce an unobstructed opening to allow access to biological fluid.

22 Claims, 11 Drawing Sheets

U.S. PATENT DOCUMENTS

| | | |
|---|---|---|
| 4,577,630 | 3/1986 | Nitzsche et al. . |
| 4,627,445 | 12/1986 | Garcia et al. . |
| 4,640,297 | 2/1987 | Bates . |
| 4,653,513 | 3/1987 | Dombrowski . |
| 4,775,361 | 10/1988 | Jacques et al. . |
| 4,838,855 | 6/1989 | Lynn . |
| 4,883,068 | 11/1989 | Dechow . |
| 4,895,147 | 1/1990 | Bodicky et al. . |
| 4,976,724 | 12/1990 | Nieto et al. . |
| 4,981,473 | 1/1991 | Rosenblatt . |
| 4,990,154 | 2/1991 | Brown et al. . |
| 5,014,718 | 5/1991 | Mitchen . |
| 5,037,431 | 8/1991 | Summers et al. . |
| 5,070,886 | 12/1991 | Mitchen et al. . |
| 5,100,427 | 3/1992 | Crossman et al. . |
| 5,165,418 | 11/1992 | Tankovich . |
| 5,201,324 | 4/1993 | Swierczek . |
| 5,231,993 | 8/1993 | Haber et al. . |
| 5,238,655 | 8/1993 | Laible et al. . |
| 5,282,822 | 2/1994 | Macors et al. . |
| 5,304,193 | 4/1994 | Zhadanov . |
| 5,318,584 | 6/1994 | Lange et al. . |
| 5,320,607 | 6/1994 | Ishibashi . |
| 5,374,556 | 12/1994 | Bennett et al. . |
| 5,487,748 | 1/1996 | Marshall et al. . |
| 5,636,640 | 6/1997 | Staehlin . |
| 5,662,127 | 9/1997 | DeVaughn . |
| 5,680,872 | 10/1997 | Sesekura et al. . |

FOREIGN PATENT DOCUMENTS

| | | |
|---|---|---|
| 0449525 | 10/1991 | European Pat. Off. . |
| 0520296 | 12/1992 | European Pat. Off. . |
| 0575952 | 12/1993 | European Pat. Off. . |
| 0671146 | 2/1995 | European Pat. Off. . |
| 0671146 | 9/1995 | European Pat. Off. . |
| 0797951 | 10/1997 | European Pat. Off. . |
| 2803345 | 6/1979 | Germany . |
| 3708031 | 11/1987 | Germany . |
| 2222251 | 2/1990 | United Kingdom . |
| 9109139 | 6/1991 | WIPO . |
| 9215863 | 9/1992 | WIPO . |
| 9303673 | 3/1993 | WIPO . |
| 9409713 | 5/1994 | WIPO . |
| 9637148 | 11/1996 | WIPO . |
| 9742882 | 11/1997 | WIPO . |
| 9742883 | 11/1997 | WIPO . |
| 9742886 | 11/1997 | WIPO . |
| 9743962 | 11/1997 | WIPO . |

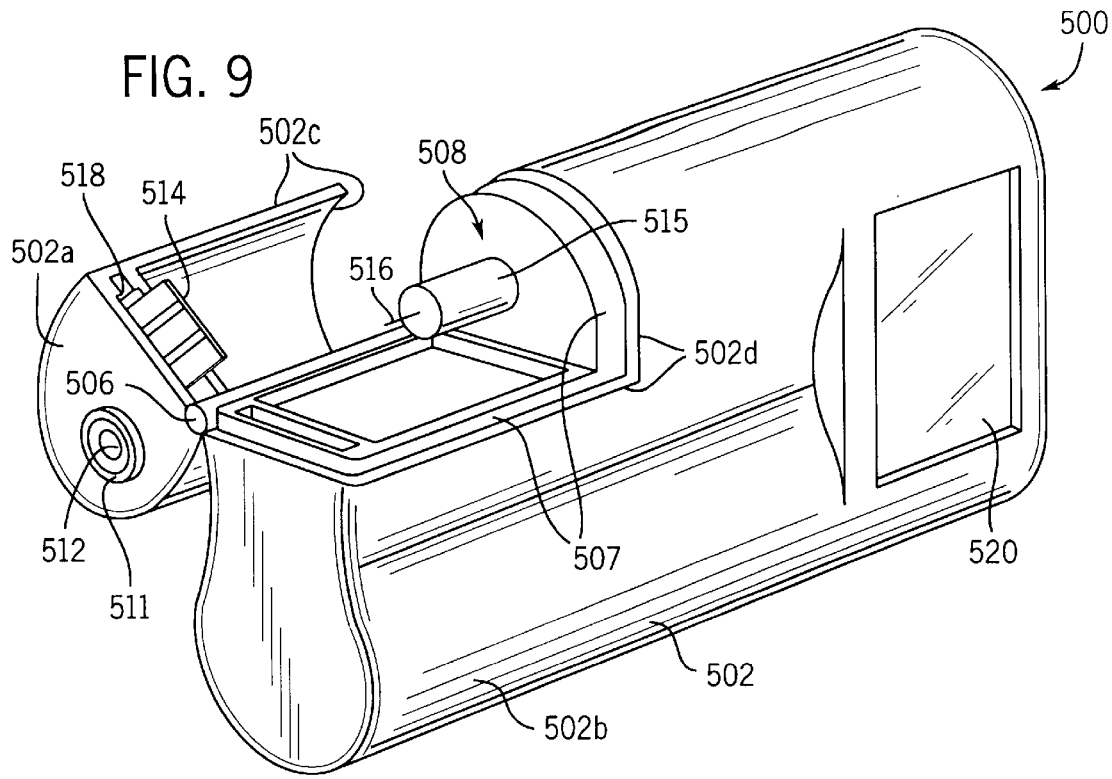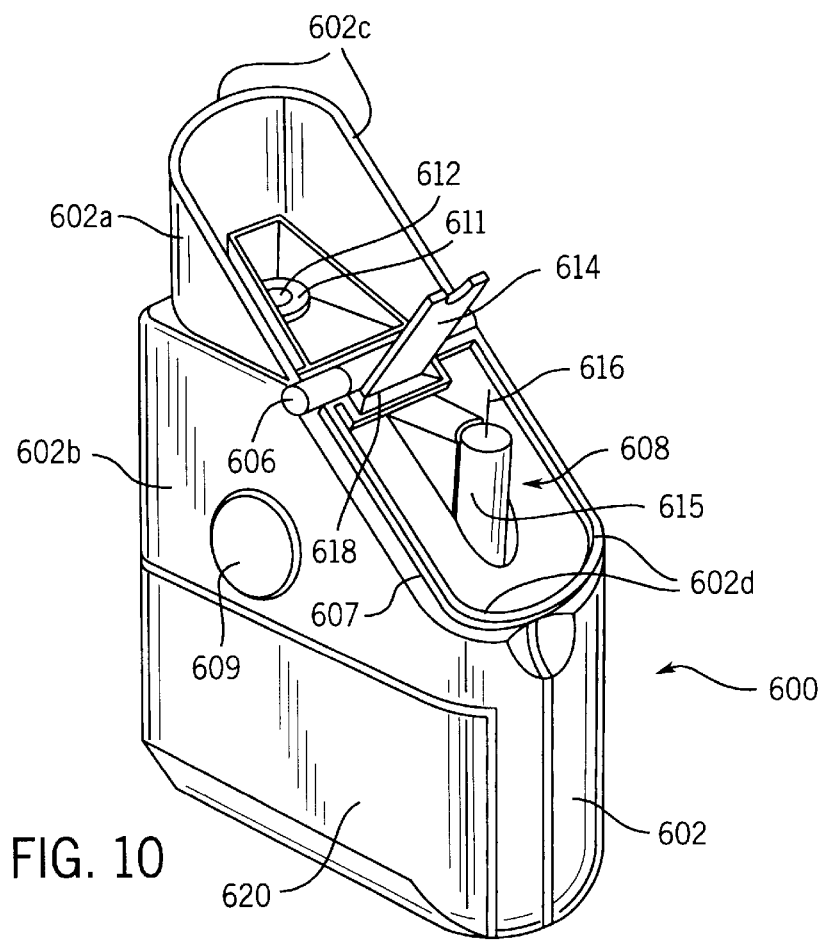

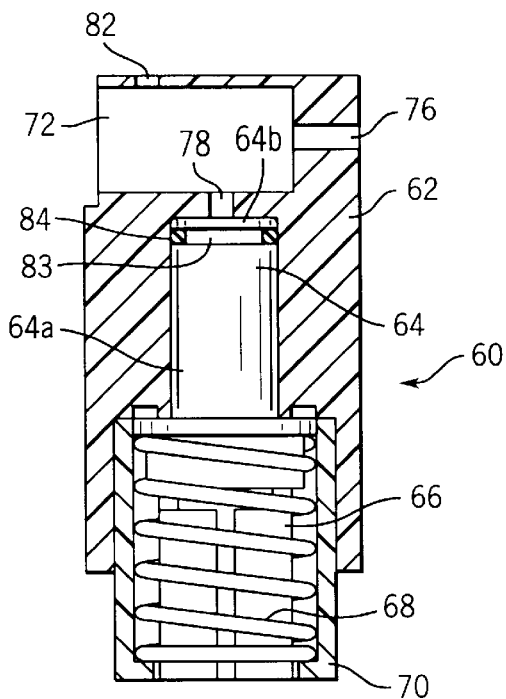
FIG. 11
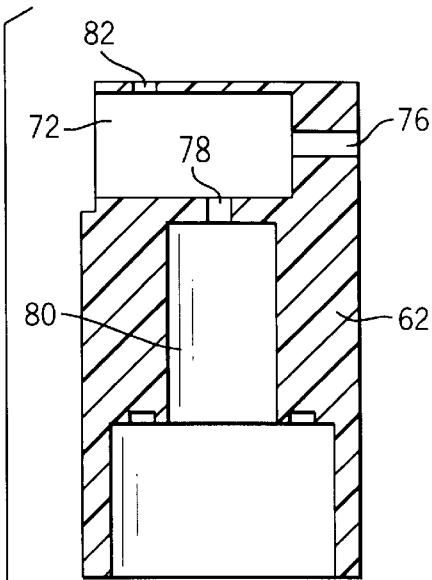
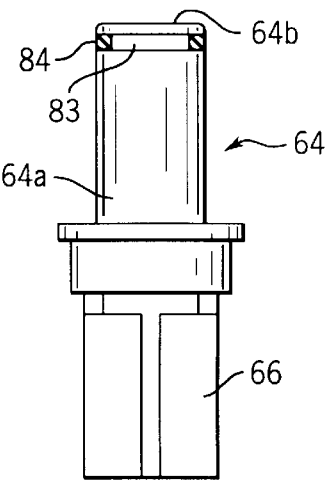
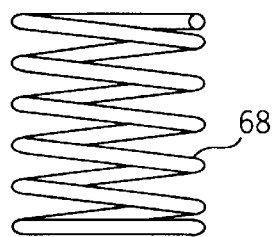
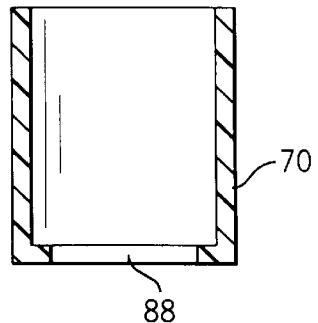
FIG. 12

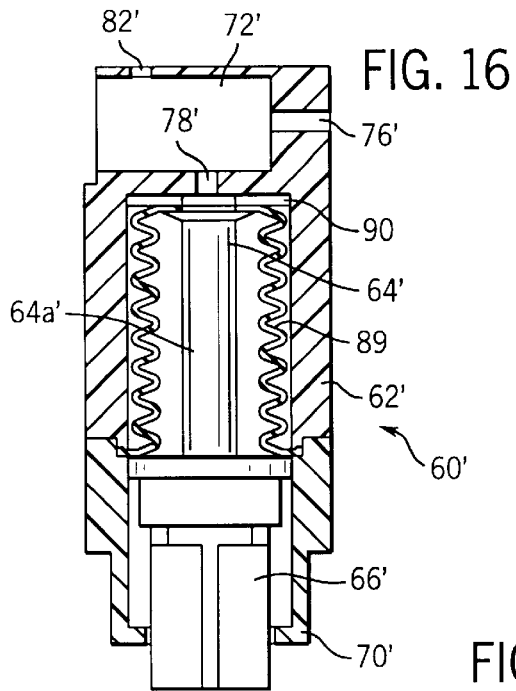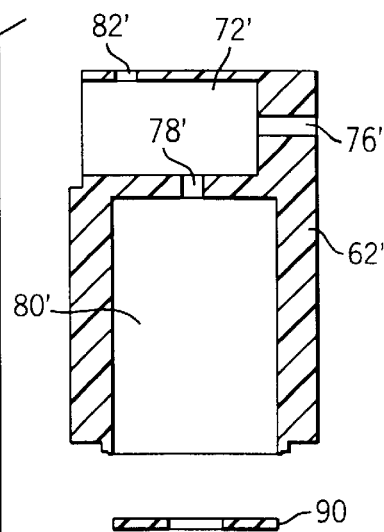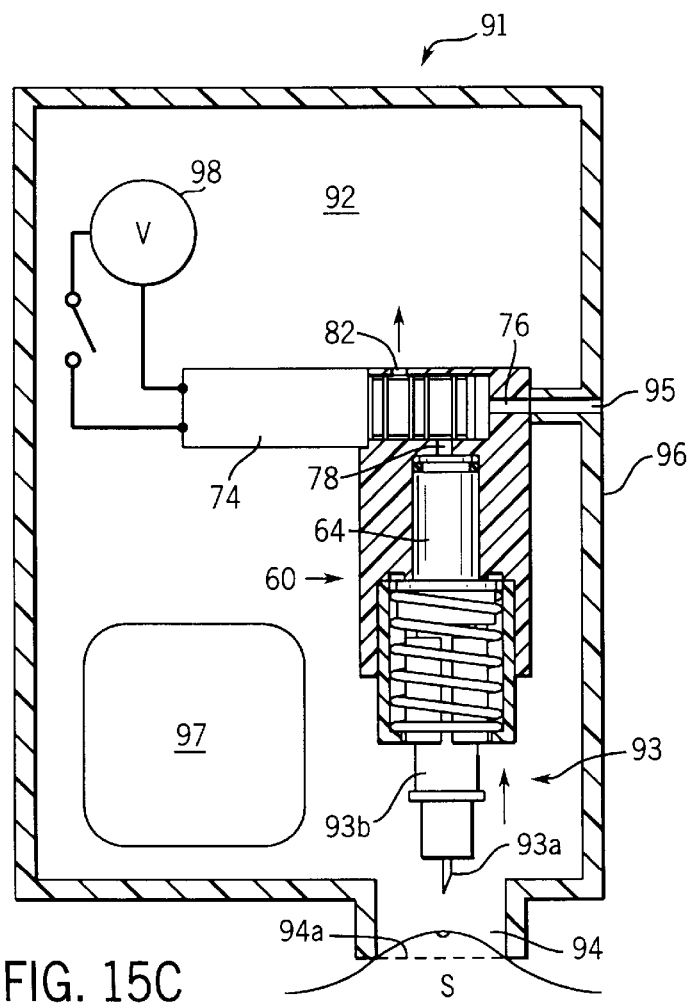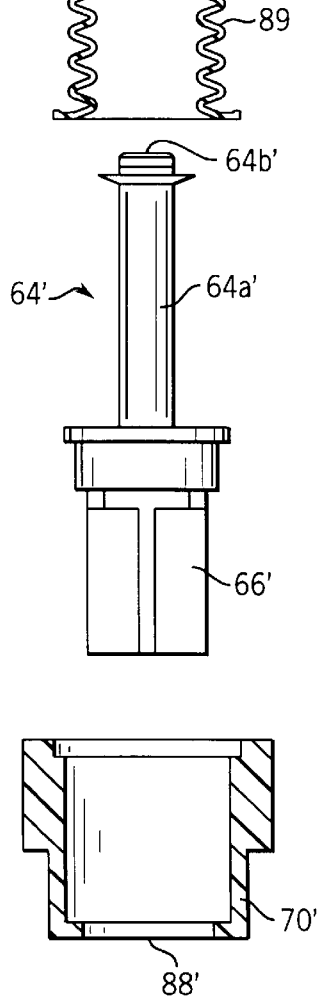

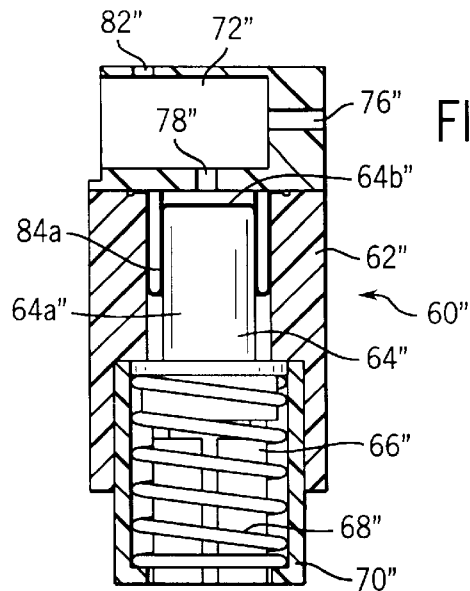
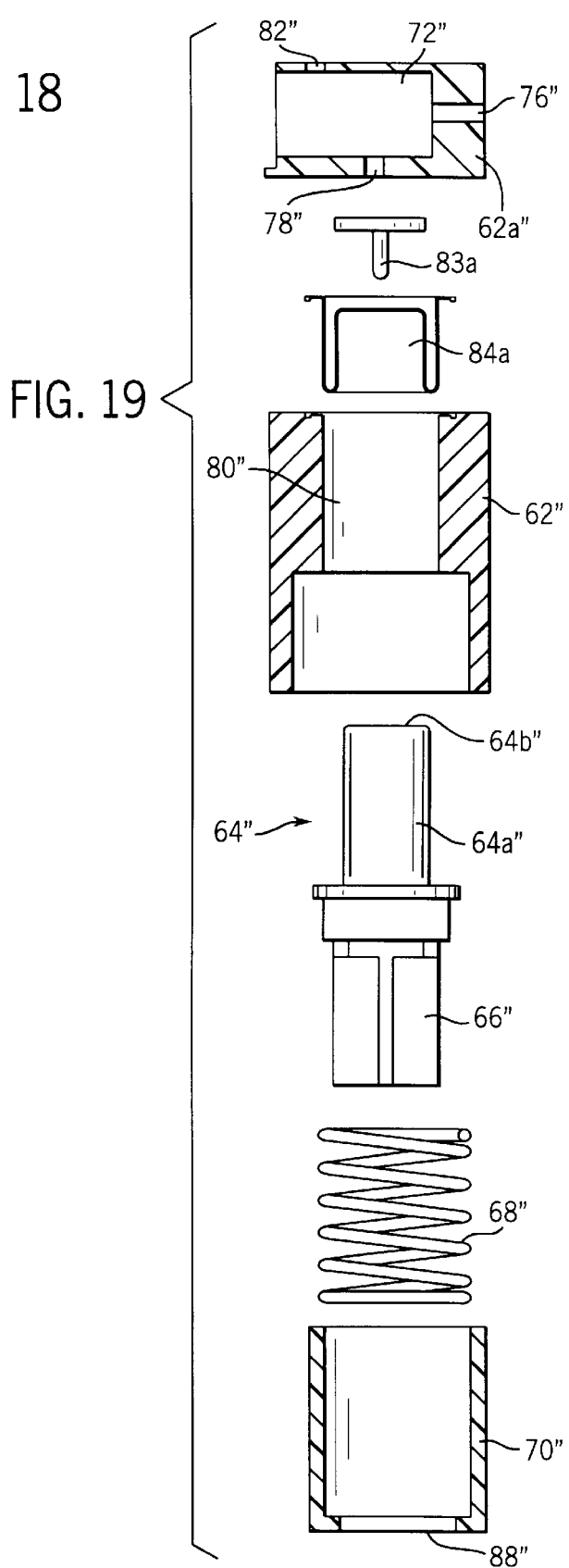

METHOD AND APPARATUS FOR OBTAINING BLOOD FOR DIAGNOSTIC TESTS

This application is a continuation-in-part of U.S. Ser. No. 08/759,698, filed Dec. 6, 1996 and a continuation-in-part of U.S. Provisional Application No. 60/036,395, filed Jan. 24, 1997.

CROSS REFERENCES TO COPENDING APPLICATIONS

This application relates to three patent applications, METHOD AND APPARATUS FOR OBTAINING BLOOD FOR DIAGNOSTIC TESTS, Attorney's Docket No. 6005.US.P2, METHOD AND APPARATUS FOR OBTAINING BLOOD FOR DIAGNOSTIC TESTS, Attorney's Docket No. 6005.US.P3, METHOD AND APPARATUS FOR OBTAINING BLOOD FOR DIAGNOSTIC TESTS, Attorney's Docket No. 6005.US.P4, filed on even-date herewith. The specifications, drawings, and claims of these applications are incorporated herein by reference. All of the foregoing applications are commonly owned by the assignee of this invention.

BACKGROUND OF THE INVENTION

1. Field of the Invention

This invention relates to a method and apparatus for obtaining samples of blood for diagnostic purposes.

2. Discussion of the Art

The prevalence of diabetes has been increasing markedly in the world. At this time, diagnosed diabetics represented about 3% of the population of the United States. It is believed that the total actual number of diabetics in the United States is over 16,000,000. Diabetes can lead to numerous complications, such as, for example, retinopathy, nephropathy, and neuropathy.

The most important factor for reducing diabetes-associated complications is the maintenance of an appropriate level of glucose in the blood stream. The maintenance of the appropriate level of glucose in the blood stream may prevent and even reverse many of the effects of diabetes.

Glucose monitoring devices of the prior art have operated on the principle of taking blood from an individual by a variety of methods, such as by needle or lancet. An individual then coats a paper strip carrying chemistry with the blood, and finally insert the blood-coated strip into a blood glucose meter for measurement of glucose concentration by determination of change in reflectance.

The medical apparatus of the prior art for monitoring the level of glucose in the blood stream required that an individual have separately available a needle or lancet for extracting blood from the individual, strips carrying blood chemistry for creating a chemical reaction with respect to the glucose in the blood stream and changing color, and a blood glucose meter for reading the change in color indicating the level of glucose in the blood stream. The level of blood glucose, when measured by a glucose meter, is read from a strip carrying the blood chemistry through the well-known process of reading reflectometers 15 for glucose oxidation.

Generally lancets comprise a blade and a pressable end opposed thereto, with the blade having an acute end capable of being thrust into skin of a human. By striking the pressable portion, the acute end of the blade will pierce the skin, for example, of the finger. The finger lancet is primarily used to obtain small volumes of blood, i.e., less than 1 mL. Diabetics use the finger lancet to obtain volumes of blood less than 25 $\mu$L for analysis for glucose. A small amount of blood for the blood test will ooze out of the skin. There are many small blood vessels in each finger so that a finger can be squeezed to cause a larger drop of blood to ooze. The finger is one of the most sensitive parts of the body; accordingly, the finger lancet leads to even more pain than what would be experienced by extracting blood via lancet at a different body site. The finger lancet presents another problem because of the limited area available on the fingers for lancing. Because it is recommended that diabetics monitor their blood glucose levels four to six times per day, the limited area on the fingers calls for repeated lancing of areas that are already sore. Because fingers are sensitive to pain, it is a recent tendency that the arm is subjected to blood sampling. See, for example, U.S. Pat. No. 4,653,513. The device of U.S. Pat. No. 4,653,513 comprises a cylindrical housing and a lancet support, which has a gasket or flexible portion slidably accommodated in the housing. Springs will retract the lancet support to thereby reduce air pressure in the housing so that it sucks a blood sample, automatically and immediately after a lancet pierces the skin. See also U.S. Pat. No. 5,320,607, which discloses a device comprising a sealed vacuum chamber in a state of preexisting reduced pressure, a support member for the sealed vacuum chamber, the support member defining a suction portion adjacent the sealed vacuum chamber, the suction portion, in cooperation with the sealed vacuum chamber, exposing an area of the skin of a patient to a reduced pressure state when the device is actuated, and means arranged within the suction portion for slightly rupturing a portion of the area of skin of the patient exposed to the reduced pressure state.

Because the blood volume requirements for a standard glucose test strip is typically 3 $\mu$L or more, an area of the body that can generate that much blood from a lancet wound must be used. It is believed, however, that improvements in glucose test strip technology will reduce the volume of blood needed to 1 to 3 $\mu$L. Because the finger is well supplied with blood and the amount of blood can be increased by squeezing the finger after lancing, the finger is the currently preferred body site for lancing, even though lancing of the finger is painful.

A less painful technique for obtaining body fluids could be found if a reliable method were found for lancing a body part that is less sensitive to pain than the finger and obtaining a useful amount of blood from that body part. A body part such as the forearm is much less sensitive to pain than the finger, but the amount of blood resulting from the lancing procedure is generally of an inadequate volume for use with current detection technology. Ways of increasing blood flow to the finger are common knowledge. The recommendation is made to diabetics to run their finger under hot water prior to lancing to improve the blood flow in the finger and the amount of blood collected from the finger. Running hot water over a body part to improve blood flow is impractical for areas such as the forearm or thigh. The availability of hot water is also a concern.

It would be desirable to develop a technique and apparatus for obtaining blood for diagnostic purposes in a painless, reliable manner.

Conventional lancing devices, such as those described in U.S. Pat. Nos. Re. 32,922, 4,203,446, 4,990,154, and 5,487,748, accept commercially available, disposable lancets. Most conventional lancing devices are not integrated with a diagnostic instrument. A conventional lancing mechanism typically consists of a housing, a guided shaft having a lancet holder at one end, a main spring (usually helical) that supplies the mechanical energy to axially accelerate the shaft, and a return spring that partially retracts the shaft after lancing has occurred. The user must first insert a lancet into the holder, then manually slide the shaft until the main spring is compressed and the shaft is locked into its "cocked" position, then place the device against the skin, then press a trigger, which releases the shaft, thereby driving the lancet into the skin. The lancet is quickly retracted from the skin by the force of the return spring.

Conventional lancing devices would have several disadvantages for an apparatus that combines the processes of lancing, fluid collecting, and analyte sensing into one automated instrument. The first disadvantage is the necessity of manually cocking the lancing mechanism prior to each use. Manual cocking is inconvenient for the user and generally adversely affects the automated characteristics of an integrated instrument. Manual cocking also prohibits rapid, sequential lancing of the target skin. Sequential lancing could increase the volume of biological fluid collected. The second disadvantage is that the mechanical trigger can be accidentally pressed by the user if the device is mishandled. Accidental triggering of the lancet could injure the user and cause technical problems within an automated lancing system. The user would be further inconvenienced by having to re-cock the mechanism after accidental triggering. The third disadvantage is that the conventional return spring is generally not able to completely retract the lancet, due to the opposing force of the main spring. Partial retraction may subject the user to accidental punctures when handling the instrument before or after use, particularly when the lancet is located near other disposable components, such as fluid sample collection strips.

It would therefore be desirable to provide a lancing device that eliminates one or more of the foregoing disadvantages.

SUMMARY OF THE INVENTION

This invention provides a method and apparatus for extracting a sample of blood from a patient for subsequent diagnostic tests, e.g., glucose monitoring. In one aspect of the invention, the method comprises the steps of:

(a) forming an unobstructed opening in the area of the skin from which the sample of blood is to be extracted; and (b) extracting the sample of blood from the unobstructed opening in the skin, with the aid of vacuum and stretching of the skin.

In a preferred embodiment of the method, step (a) is preceded by the step of increasing the availability of blood in the portion of the skin from which the sample is to be extracted. In this preferred embodiment, the availability of blood in the portion of the skin from which the sample is to be extracted can be increased by means of a vacuum, which is applied to the surface of the skin in the vicinity of the opening prior to forming the opening in the skin. The vacuum causes the portion of the skin in the vicinity of the blood extraction site to become engorged with blood. The vacuum also causes the portion of the skin in the vicinity of the blood extraction site to become stretched. An opening in this stretched portion of skin can be formed with a cutting or puncturing device, e.g., a lancet, or other device capable of forming an opening in the skin, e.g., a laser or a fluid jet. If a cutting or puncturing device is used to form the opening, it must be retracted from the opening prior to the step of extracting the sample of blood from the opening. This retraction will allow the unrestricted flow of blood through the opening. After the opening is formed, a vacuum is used to aid in extracting the sample of blood from the opening in the skin. The sample can be analyzed from the drops of blood that collect on the surface of the skin at the site of the opening by applying the blood directly to a glucose detector. It is preferred, however, that the sample be collected in such a manner, e.g., via a capillary tube, that it can be analyzed by conventional diagnostic devices, such as, for example, a biosensor. In another preferred embodiment, the sample can be collected in a collection zone that is integrated with a conventional diagnostic device, e.g., a biosensor.

In an alternative of the aforementioned preferred embodiment, the availability of blood in the area of the skin from which the sample is to be extracted can be increased by means of applying thermal energy to that area of skin. The thermal energy causes the blood in that area of the skin to flow more rapidly, thereby allowing more blood to be collected per given unit of time. In this alternative embodiment, steps (a) and (b) can be carried out in the same manner as they were carried out in the aforementioned preferred embodiment.

In another aspect of the invention, an apparatus for collecting a sample of body fluid for analysis in a diagnostic test, e.g., blood, is provided. In a preferred embodiment, the apparatus comprises:

(a) a housing;

(b) a device for forming an unobstructed opening in an area of skin from which said sample is to be extracted, preferably a lancing assembly; and (c) a vacuum pump.

It is also possible to dispense with the housing. However, the housing is preferred for the convenience of the patient and the protection of the components.

The vacuum pump requires a source of power. If the apparatus includes a housing, the source of power can be disposed within the housing. Alternatively, the source of power can be external to the housing.

The preferred device for forming an unobstructed opening in the area of the skin from which the sample of blood is to be extracted is a lancing assembly, which comprises a lancet for forming an opening in the skin. Alternatively, the unobstructed opening in the skin can be formed by a laser or a fluid jet.

The vacuum pump can serve the dual purposes of (1) stretching the skin and (2) enhancing the extraction of the sample of blood from the unobstructed opening in the skin. Preferably, the vacuum pump can serve the triple purposes of (1) stretching the skin, (2) increasing the availability of blood to the area of the skin from which the sample is to be extracted, and (3) enhancing the extraction of the sample of blood from the unobstructed opening in the skin. Preferably, the housing further contains electronics having programmed instructions to switch the vacuum pump on and off to maintain the desired level of vacuum.

The apparatus preferably contains valves, such as, for example, solenoid valves, for triggering the lancet of the lancing assembly and releasing the vacuum at the conclusion of the blood extraction procedure. The apparatus can optionally contain a heating element to increase the availability of blood to the area of the skin from which the sample is to be extracted. The apparatus can also contain a glucose detector integrated with the apparatus, e.g., a biosensor, to analyze the sample of blood collected by the apparatus.

In another aspect of this invention, a lancing assembly that uses differential gas pressure to thrust a lancet into skin tissue has been developed. This lancing assembly effectively utilizes low-pressure gas, which is preferably provided by the aforementioned vacuum pump, and high-pressure gas, which is preferably provided by ambient air surrounding the apparatus, to thrust the lancet, puncture the skin, and then retract the lancet from the skin to produce an unobstructed opening to allow access to biological fluid. The lancing assembly eliminates the need to manually force the lancing mechanism into a latched, or "cocked", position prior to each use, and also eliminates the need for a mechanical trigger to release the latch to allow the lancet to be thrust into the skin. Elimination of the requirement to manually cock the lancing mechanism allows the lancing assembly to be controlled exclusively by electronic means. Such means of control is desirable when used in conjunction with an automated instrument, or when a continuous series of lancing steps is desired.

The lancing assembly that utilizes differential gas pressure comprises:

(a) a holder for holding a lancet assembly;
(b) a means for providing sufficient force to cause the holder to be maintained in a position whereby a lancet assembly in the holder would be positioned away from the skin of the patient; and
(c) a means for allowing a gas to provide sufficient force to overcome the force provided by the holder maintaining means, whereby the gas causes the holder to be moved to a position whereby a lancet in the holder would be able to pierce the skin of the patient.

In one embodiment, the lancing assembly comprises a housing, a lancet holder, a piston for moving the lancet holder, a bore in which the piston moves toward and away from the target skin tissue, a means for biasing the piston, e.g., a return spring or a bellows, away from the target skin tissue, and a cap. The housing has a manifold into which a three-way valve can be fitted. The three-way valve selectively allows high-pressure air from a source external to the housing to pass through an inlet port to a bore port, thereby causing the level of pressure in the bore to increase. The air pressure in the bore thrusts the piston toward the target skin tissue while simultaneously compressing the piston biasing means. The piston is halted by the cap or by a structure in the instrument designed to limit the penetration depth of the lancet in the skin. The three-way valve then directs the air in the bore to flow out through an exit port to a source of low-pressure air, e.g., an evacuated air cavity in the apparatus, thereby causing the level of pressure in the bore to decrease, and consequently allowing the piston biasing means to force the piston back to its pre-thrust position in the bore.

The method and apparatus of this invention provide several advantages over the methods and apparatus of the prior art. First, a sufficient amount of blood can be extracted from parts of the body, other than the finger, for conducting glucose monitoring tests. Second, by rendering other parts of the body suitable for extracting blood, the use of a painful finger lance can be avoided. Third, by increasing the availability of blood at the site where the blood is to be extracted, the period of time required for extracting the sample can be reduced. Because of these advantages, the diabetic patient is more likely to monitor glucose levels in the blood at the intervals prescribed by his doctor.

BRIEF DESCRIPTION OF THE DRAWINGS

FIG. 2 also illustrates the spatial relationship between the nosepiece. of lancing assembly and a glucose detector, e.g., a biosensor.

FIG. 9 is a perspective view of an embodiment of the apparatus of this invention. In this figure, the housing of the apparatus is open.

FIG. 10 is a perspective view of an embodiment of the apparatus of this invention. In this figure, the housing of the apparatus is open.

FIG. 11 is an elevational view, in cross section, of one embodiment of the lancing assembly of this invention in assembled configuration.

FIG. 12 is an exploded view, in cross section, of the lancing assembly of FIG. 11.

FIGS. 15A, 15B, and 15C are schematic diagrams illustrating the lancing assembly of this invention in the pre-lancing position, the lancing position, and the post-lancing position, respectively.

FIG. 16 is an elevational view, in cross section, of another embodiment of the lancing assembly of this invention in assembled configuration.

FIG. 17 is an exploded view, in cross section, of the lancing assembly of FIG. 16.

FIG. 18 is an elevational view, in cross section, of another embodiment of the lancing assembly of this invention in assembled configuration.

FIG. 19 is an exploded view, in cross section, of the lancing assembly of FIG. 18.

DETAILED DESCRIPTION

Figure 1:
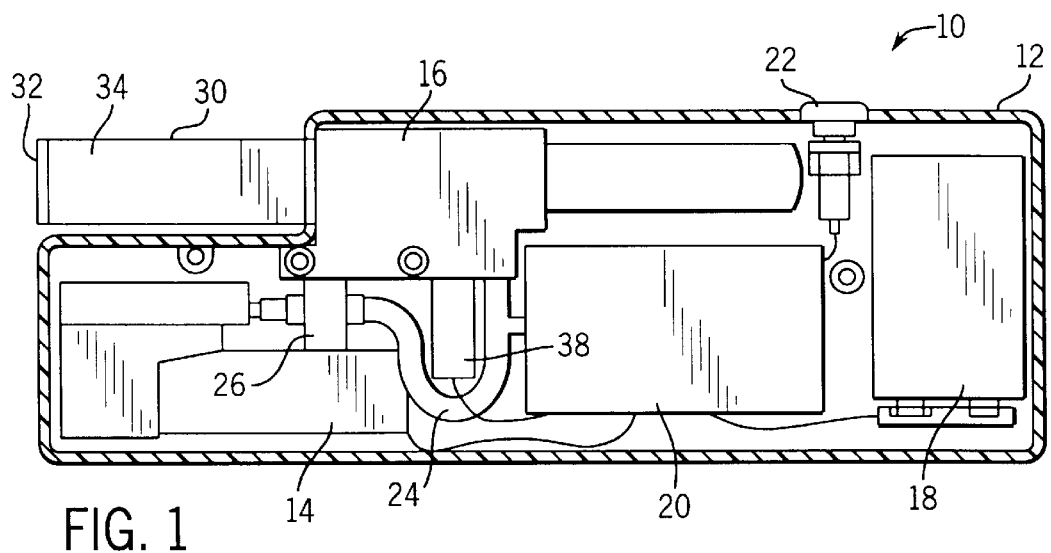
FIG. 1 is a plan view of the components of a preferred embodiment of the apparatus of this invention. In this Figure, the cover of the housing is removed.

The embodiments of this invention require the following steps to carry out the function of obtaining a sample of blood for carrying out a diagnostic test, e.g., glucose monitoring:

(a) forming an unobstructed opening in the area of the skin from which the sample of blood is to be extracted; and (b) extracting the sample of blood from the unobstructed opening in the skin, with the aid of a vacuum and a stretching of the skin.

The step of forming an unobstructed opening in the area of the skin from which the sample of blood is to be extracted is carried out by a piercing device or some other type of device capable of forming an unobstructed opening in the skin. Piercing devices suitable for this invention include, but are not limited to, mechanical lancing assemblies. Other type of device capable of forming an unobstructed opening in the skin include, but are not limited to, lasers and fluid jets. Other types of devices capable of forming an unobstructed opening in the skin can be used, and this disclosure should not be construed so as to be limited to the devices listed. Mechanical lancing assemblies are well-known in the art. These assemblies comprise include standard steel lancets, serrated devices, and multiple tip devices. The lancets can be made from metal or plastic. Multiple tip devices provide redundancy, which can reduce the number of failures and increase the volume of blood extracted.

Lasers suitable for forming an unobstructed opening in the skin to draw blood are also well-known in the art. See for example, U.S. Pat. Nos. 4,775,361, 5,165,418, 5,374,556, International Publication Number WO 94/09713, and Lane et al. (1984) IBM Research Report—"Ultraviolet-Laser Ablation of Skin", all of which are incorporated herein by reference. Lasers that are suitable for forming an unobstructed opening in the skin the skin include Er:YAG, Nd:YAG, and semiconductor lasers.

Fluid jets suitable for forming an unobstructed opening in the skin employ a high pressure jet of fluid, preferably a saline solution, to penetrate the skin.

Regardless of what type of device is utilized to form an unobstructed opening in the skin, the opening formed by the device must be unobstructed. As used herein, the term "unobstructed" means free from clogging, hampering, blocking, or closing up by an obstacle. More specifically, the expressions "unobstructed opening in the area of the skin from which the sample is to be extracted", "unobstructed opening in the skin", and the like are intended to mean that the portion of the opening below the surface of the skin is free from any foreign object that would clog, hamper, block, or close up the opening, such as, for example, a needle of any type. For example, if a lancet is used to form the opening, it must be retracted from the opening prior to the commencement of the extraction of blood. Because lasers and fluid jets do not require contact with the skin to form openings in the skin, these types of devices typically provide unobstructed openings. However, these expressions are not intended to include foreign objects at the surface of the skin or above the surface of the skin, such as, for example, a glucose monitor. This feature, i.e., the unobstructed opening, can be contrasted with the opening used in the method and apparatus described in U.S. Pat. No. 5,320,607, in which the piercing and cutting means remains in the skin during the duration of the period of blood extraction. By leaving the opening unobstructed, blood can be extracted much more rapidly from the opening than it would be extracted if the piercing and cutting means were allowed to remain in the opening. In addition, the requirement of an unobstructed opening exposes the body to a foreign object either not at all or for only a very short period of time, which is welcomed by the patient.

The step of extracting the sample of blood from the opening in the skin is carried out by a combination of extraction enhancing elements. Extraction enhancing elements suitable for use in this invention include, but are not limited to, vacuum, skin stretching elements, and heating elements. It has been discovered that when these elements are used in combination, the volume of blood extracted is greatly increased, particularly when a vacuum is applied in combination with skin stretching. In this combination, the vacuum not only causes the blood to be rapidly removed from the unobstructed opening by suction, it also causes a portion of the skin in the vicinity of the opening to be stretched. Stretching of the skin can be effected by other means, such as mechanical means or adhesives. Mechanical means include devices for pinching or pulling the skin; adhesives bring about stretching of the skin by means of pulling. It is preferred to use a vacuum to effect stretching of the skin. Like a vacuum, a heating element operates more effectively in combination with other techniques, e.g., stretching of the skin.

In the preferred embodiment of this invention, step (a), the step of forming the unobstructed opening, is preceded by the step of increasing the availability of blood at the area of the skin from which the sample is to be extracted. The availability of blood at a given area of the skin can be increased by at least two methods. In one method, a vacuum can be used to cause blood flowing through blood vessels to pool in the area of the skin where the vacuum is applied. In another method, heat can be used to cause blood flowing through blood vessels to flow more rapidly in the area of the skin where heat is applied, thereby allowing a greater quantity of blood to be extracted from the blood extraction site per unit of time. Although the step of increasing the availability of blood in the vicinity of the blood extraction site is not required, the employment of this step can result in a greater volume of blood extracted. Elements for increasing the availability of blood at a blood extraction site that are suitable for use in this invention include, but are not limited to, vacuum, localized heating element, skin stretching element, and chemicals. As stated previously, applying a vacuum to the area of the skin from which blood is to be extracted can increase blood availability under and within the skin at the application site. The vacuum can also be used to stretch the skin upwardly into a chamber, thereby increasing pooling of blood under and within the skin. This combination of vacuum and skin stretching can be an extension of the combination used to extract blood from the opening in the skin, as previously described. It is well known that heat can increase perfusion on the large scale of a limb or a finger. Chemical means, such as histamine, can be used to cause a physiological response to increase perfusion under and within the skin.

In the preferred embodiments of the invention, the extracted blood is also collected. The step of collecting the sample of blood can be carried out in a variety of ways. For example, the blood can be collected in capillary tubes or absorbent paper. Alternatively, the blood can be allowed to remain in the lancet assembly, from which it can used directly in a diagnostic test. Most preferably, the sample of blood is collected on the application zone of a glucose detector, from where it can be used directly to provide an indication of the concentration of glucose in the blood. Regardless of the manner in which the blood sample is collected, the sample can be analyzed at a time later than the time of collection or at a location remote from the location of collection or both.

A preferred embodiment of the invention will now be described in detail. Blood extraction device 10 comprises a housing 12. Disposed within the housing 12 are a vacuum pump 14, a lancing assembly 16, a battery 18, and electronics 20. A switch 22 is provided to activate electronics 20.

The housing 12 is preferably made from a plastic material. It is preferably of sufficient size to contain all of the components that are required for forming an unobstructed opening in the area of the skin from which the sample of blood is to be extracted, extracting the sample of blood from the unobstructed opening in the skin, preferably with the aid of a vacuum and a stretching of the skin, and collecting the extracted sample in an amount sufficient to carry out a diagnostic test. Methods of preparing the housing 12 are well-known to one of ordinary skill in the art. As stated previously, the housing 12 is not required, but is preferred for the convenience of the patient and the protection of the components.

The vacuum pump 14 must be capable of providing a vacuum that will provide sufficient suction to stretch the portion of the skin in the region from which the sample of blood is to be extracted. Typically, the portion of stretched skin is raised a distance of 1 to 10 mm, preferably 3 to 5 mm, from the plane of the body part of which it is a portion. As the suction provided by the vacuum pump 14 is stretching the appropriate portion of skin, the suction provided by the vacuum pump 14 also causes the stretched portion to become engorged with blood. The level of suction provided must be sufficient to cause a relatively large volume of blood to become engorged at the point that the vacuum is applied. The vacuum pump 14 must also be capable of providing sufficient suction to extract blood from the opening in the skin at a rate sufficient to extract at least 1 $\mu$L of blood within a period of five minutes. A vacuum pump 14 that is suitable for the device of this invention can be a diaphragm pump, a piston pump, a rotary vane pump, or any other pump that will perform the required functions set forth previously. Typically, the vacuum pump 14 employs a self-contained permanent magnet DC motor. Vacuum pumps that are suitable for this invention are well-known to those of ordinary skill in the art and are commercially available. A vacuum pump suitable for use in the present invention is available from T-Squared Manufacturing Company, Nutley, N.J., and has the part number T2-03.08.004.

The vacuum pump 14 is preferably capable of providing a pressure of down to about −14.7 psig, and is more preferably operated at from about −3.0 psig to about −10.0 psig. The area of the skin subjected to vacuum preferably ranges up to about 50 cm$^2$, more preferably from about 0.1 to about 5.0 cm$^2$. The period of vacuum application prior to forming the opening in the skin, i.e., for increasing the availability of blood to the application site, preferably ranges up to about 5 minutes, preferably from about 1 to about 15 seconds. The period of vacuum application subsequent to forming the opening in the skin, i.e., for aiding in the extraction of blood from the unobstructed opening, preferably ranges up to about 5 minutes, preferably from about 1 to about 60 seconds. The vacuum provided by the vacuum pump 14 can be continuous or pulsed. A continuous vacuum is preferred for the reason that it requires fewer components than does a pulsed vacuum. It is preferred that the vacuum applied not cause irreversible damage to the skin. It is preferred that the vacuum applied not produce bruises and discolorations of the skin that persist for several days. It is also preferred that the level of vacuum applied and duration of application of vacuum not be so excessive that it causes the dermis to separate from the epidermis, which results in the formation of a blister filled with fluid.

The vacuum pump feature offers significant advantages over the method and apparatus described in U.S. Pat. No. 5,320,607, in which a sealed vacuum chamber in a state of preexisting reduced pressure is used. The use of a vacuum pump provides the user with greater control of blood extraction conditions than does a sealed vacuum chamber in a state of preexisting reduced pressure. For example, if the vacuum is insufficient, energy can be provided to the vacuum pump to bring about a higher level of vacuum, thereby providing greater suction.

The lancing assembly 16 comprises at least one lancet. Standard lancets can be used in the lancing assembly of this invention. Narrow gauge (28 to 30 gauge) lancets are preferred. Lancets suitable for this invention can be made from metal or plastic. Lancets suitable for this invention can have single points or multiple points. The depth of penetration of the lancet preferably ranges from about 0.4 to about 2.5 mm, more preferably from about 0.4 to about 1.6 mm. The length of the lancet or lancets preferably ranges from about 1 mm to about 5 mm. The lancing assembly is preferably located so that the user can easily replace used lancets. The lancet of the lancing assembly 16 can be cocked manually or automatically, e.g., by means of a vacuum-actuated piston or diaphragm. The lancet of the lancing assembly 16 can be triggered by manually or automatically, e.g., by means of a vacuum-actuated piston or diaphragm.

Lancing assemblies are well-known in the art. Representative examples of lancing assemblies suitable for this invention are described in U.S. Pat. Nos. Re. 32,922, 4,203, 446, 4,990,154, and 5,487,748, all of which are incorporated herein by reference. A particularly suitable lancing assembly for this invention is described in U.S. Pat. No. Re. 32,922. However, any lancing assembly selected should operate in conjunction with the other features of the apparatus of this invention. For example, if a vacuum is employed, the lancing assembly must be designed so that a vacuum can be formed and drawn through the assembly. The lancing assembly can be designed to allow automatic cocking and automatic triggering of the lancet.

While conventional lancing assemblies are suitable for use in this invention, a lancing assembly that utilizes differential gas pressure to thrust a lancet into skin tissue has been developed for use with this invention. As used herein, the expression "differential gas pressure" means the difference in gas pressure between a gas source at a high pressure, e.g., ambient air or pressurized air, and a gas source at a low pressure, e.g., air within a vacuum. In any event, the pressure of a gas source at high pressure exceeds the pressure of a gas source at low pressure.

FIGS. 11, 12, 13, and 14 illustrate an embodiment of a lancing assembly suitable for use in this invention. In this embodiment, the gas is air. However, it should be noted that other gases, e.g., nitrogen, carbon dioxide, can be used in place of air for the gas source at low pressure, the gas source at high pressure, or both. The lancing assembly 60 of this embodiment comprises a housing 62, a piston 64 having a lancet holder 66, a lancet assembly 67 comprising a lancet 67a inserted into a body 67b, a piston biasing means 68, which, in this embodiment, is a return spring, and a cap 70. The housing 62 has a manifold 72 into which a three-way valve 74 can be fitted. See FIGS. 13 and 14 for manner of positioning the three-way valve 74 in the manifold 72. The three-way valve 74 selectively allows air from a source external to the housing 62 to pass through an inlet port 76 to a bore port 78, thereby causing the level of pressure in the bore 80 to increase. The increased pressure in the bore 80 causes the piston 64 to be thrust toward the target skin tissue while simultaneously compressing the return spring 68. The piston 64 is halted by the cap 70 or by another structure designed to limit the penetration depth of the lancet 67a in the skin. Such other structure can be a glucose detector in the form of a test strip, which will be described later, or a lancet stop, such as that designated by reference numeral 39 in FIG. 2. The three-way valve 74 then directs the air in the bore 80 to flow out through an exit port 82 to a source of low-pressure air, e.g., an evacuated air cavity in the apparatus, thereby causing the level of pressure in the bore 80 to decrease, and consequently allowing the return spring 68 to force the piston 64 back to its pre-thrust position in the bore 80.

Proper sizing of the components is needed to satisfy both the dimensional limitations of the apparatus and the performance requirements of the lancing process, as explained further below. The lancing assembly of this invention occupies no more space than a conventional spring-powered device and typically requires less distance for the lancet to travel.

The bore 80, typically cylindrical in shape, is the chamber in which differential air pressure is generated to thrust the piston 64 toward the target skin tissue. The bore 80 also functions to guide the piston 64 toward the target skin tissue, while providing a low-friction pneumatic seal against o-ring 84. The o-ring 84 is desirable for preventing high-pressure air from leaking out of the bore 80 during the lancing procedure, because the leakage of high-pressure air will decrease the level of air pressure in the bore 80, with the result that the thrusting speed of the piston 64 would be reduced. The manifold 72 is shaped to fit the three-way valve 74, which selectively connects bore port 78 to either inlet port 76 or exit port 82 to direct the flow of air to or from the bore 80. The exit port 82 is typically plumbed to a source of low-pressure air. The inlet port 76 is typically plumbed to a source of air pressure higher than that of the low-pressure air source. The ports 76, 78, and 82 are positioned to communicate with corresponding ports of the three-way valve 74, and are preferably sized to cause less flow resistance than the ports on the three-way valve 74.

The piston 64 is the moving component of the lancing assembly 60. It is preferably cylindrical in shape, and has a lancet holder 66 and a circumferential gland 83 for a standard o-ring 84. The lancet holder 66 is designed to securely mount a disposable lancet assembly 67, which is inserted by the user in the same manner as is used with a conventional lancing device. The lancet assembly 67 comprises a lancet 67a, which is inserted into a molded plastic body 67b. The function of the o-ring 84 is to act as a seal to maintain air pressure in the bore 80 during lancing. The o-ring should cause negligible sliding friction force along the bore 80 (negligible compared to pressure forces acting on the piston 64). The length of the shaft 64a of the piston 64 is chosen to provide a desired stroke distance, typically 5 mm to 25 mm. The major dimension of the top surface 64b of the piston 64, typically 5 mm to 10 mm in diameter for a cylindrically-shaped piston, is chosen to provide adequate surface area for pressure forces to thrust the piston 64 and the lancet assembly 67.

The return spring 68, typically a metal helical spring, is compressed between the piston 64 and the cap 70. The spring 68 forces the piston 64 to its maximum depth in the bore 80 when substantially no differential air pressure exists in the bore 80. This action properly positions the piston 64 to begin the lancing process. This position of the piston 64 is the position in which the piston 64 is furthest away from the target skin tissue when the apparatus is placed against the target skin tissue. The spring 68 also retracts the lancet assembly 67 in the lancet holder 66 away from the target skin tissue at the end of the lancing process. The spring force must be sufficient to overcome the weight of the piston/lancet system plus the sliding friction of the o-ring 84.

The cap 70 is securely positioned in the housing 62. The cap 70 properly positions the return spring 68 while providing sufficient radial clearance for the spring 68 to compress freely. The cap 70 has a passage 88 through which the lancet holder 66 can move. The cap 70 can also function to help guide the piston 64 toward the target skin tissue.

FIGS. 16 and 17 illustrate another embodiment of the lancing assembly. In these figures, prime reference numerals (i.e., reference numerals 60', 62', 64', 64a', 64b', 66', 70', 72', 76', 78', 80', 82', 88') indicate components that are identical or at least substantially similar to components designated by the same reference numerals, but with no prime marking (i.e., reference numerals 60, 62, 64, 66, 70, 72, 76, 78, 80, 82, 88 ) in FIGS. 11 and 12. In FIGS. 16 and 17, bellows 89, typically a cylindrical molded elastomer, functions as both the pneumatic seal for bore 80' and the means for biasing piston 64'. The bellows 89 effectively replaces the o-ring seal 84 and the return spring 68 shown in FIGS. 11 and 12. To accommodate the bellows 89, the shaft 64a' of the piston 64' must have a radial cross-section dimension sufficiently smaller than that of the bore 80' to provide sufficient clearance for the bellows 89. A plate 90 fastens and seals the bellows 89 to the shaft 64a' of the piston 64', and provides a means of guiding the piston 64' through the bore 80'. A cap 70' and a housing 62' are shaped to fasten and seal the base of the bellows 89 as shown. This embodiment can be used in a manner identical to the embodiment shown in FIGS. 11, 12, 13, 14, 15A, 15B, and 15C. It is clear that the embodiment employing the bellows 89 offers the potential advantage of reduced sliding friction when compared to the embodiment employing the o-ring 84. The bellows does not rub against the surface of the bore in the manner that the o-ring does; therefore, the bellows may result in reduced friction force. The friction force has the undesired effect of reducing the speed of the piston. It is also clear that the bellows requires less dimensional tolerance to be accommodated in the bore 80' than is required to accommodate the o-ring 84 in the bore 80. The bellows does not need to be precisely fitted into the bore, as does the o-ring. If the bore fits too tightly around the o-ring, then excessive sliding friction may result. It the bore fits too loosely around the o-ring, then excessive air leakage may result. By using the bellows in place of the o-ring, the manufacturing tolerances in the bore can be relaxed, with the result that manufacturing costs will be reduced and fewer parts will be rejected. The bellows 89 is preferably made of a material having sufficient stiffness and sufficient flexibility so that the bellows can perform the following functions: (1) act as a seal; (2) resist radial collapse under pressure; (3) allow the lancing assembly to retract to its initial pre-thrust position after the thrusting step; and (4) have its force overcome by differential gas pressure during operation.

FIGS. 18 and 19 illustrate another embodiment of the lancing assembly. In these figures, double prime reference numerals (i.e., reference numerals 60", 62", 64", 64a", 64b", 66", 68", 70", 72", 76", 76", 78", 80", 82", 88") indicate components that are identical or at least substantially similar to components designated by the same reference numerals, but with no prime marking (i.e., reference numerals 60, 62, 64, 66, 70, 72, 76, 78, 80, 82, 88) in FIGS. 11 and 12. In FIGS. 18 and 19, a diaphragm 84a, typically a molded elastomer, functions as the pneumatic seal for bore 80". The diaphragm 84a, in effect, replaces the o-ring seal 84 shown in FIGS. 11 and 12. The diaphragm 84a is fixed to the housing 62" and to the shaft 64a" of the piston 64" and can flex within the bore 80" when the shaft 64a" of the piston 64" moves axially in the bore 80". To accommodate the diaphragm 84a, the shaft 64a" of the piston 64" must have a radial cross-section dimension sufficiently smaller than that of the bore 80" to provide sufficient clearance for the diaphragm 84a. In addition, the housing 62" and the top 62a" of the housing must have assembly features to which the diaphragm 84a can be installed. The assembly features must also effectively seal the diaphragm 84a between the housing 62" and the top 62a" of the housing. The diaphragm 84a is preferably fastened to the shaft 64a" of the piston 64" by means of a fastener 83a. This embodiment can be operated in a manner identical to that of the embodiment shown in FIGS. 11–17. The diaphragm 84a is preferably made of a material having sufficient strength and flexibility to perform the following functions: (1) act as a seal; (2) resist rupture under pressure during operation of the lancing assembly; (3) allow the lancing assembly to thrust a lancet into the skin of a patient; and (3) allow the lancing assembly to retract to its initial pre-thrust position after the thrusting step.

The components of the lancing assemblies in FIGS. 11–19 must be of a shape and size to conform with the dimensional envelope available for the lancing assembly. Proper design of the components is also an important factor in achieving acceptable lancing results in the skin. Other important factors are the performance of the three-way valve (i.e., valve flow resistance and switching time) and the air pressure environment in which the lancing assembly operates, as discussed below. The components for constructing the lancing assembly are commercially available, and one of ordinary skill in the art would be expected to have sufficient ability to select the proper components from commercially available sources.

Lancing results are believed to be influenced by three main parameters: (1) lancet speed during impact with the skin, (2) inertial mass of the lancet/piston combination of the lancing assembly, and (3) shape and size of the lancet needle. The third parameter is not addressed by the lancing assembly of this invention because the assembly is expected to function with most commercially available lancet assemblies, such as the "BD ULTRA-FINE" (Becton-Dickinson) and the "ULTRATLC" (MediSense) brands. The first and second parameters are greatly affected by the geometrical shapes and weights of the components in the lancing assembly, although the precise influence of lancet speed and inertial mass on lancing performance are not well understood. However, good lancing performance has been observed with conventional devices, which have an inertial mass typically from 1.0 gram to 2.0 grams and deliver a peak lancet speed ranging from 3 m/sec to 5 m/sec.

A general mathematical expression that relates the lancet speed to the design of the lancing assembly and the pressure environment can be formulated from physical laws as follows:

$$M^*a(t) = A^*[P_c(t) - P_v(t)] - K_s^*[x(t) + X_s] - Ff(t)$$

where

| | | |
|---|---|---|
| t | = | elapsed time |
| M | = | total inertial mass (piston + lancet assembly) |
| a(t) | = | translational acceleration of the lancet at time = t |
| $P_c(t)$ | = | air pressure acting on the top surface of the piston at time = t |
| $P_v(t)$ | = | air pressure opposing the action of the piston at time = t |
| A | = | projected surface area of the piston acted upon by $P_c(t)$ and $P_v(t)$ |
| $K_s$ | = | spring rate constant of the return spring |
| x(t) | = | translational displacement of the lancet at time = t |
| $X_s$ | = | initial displacement of the return spring |
| Ff(t) | = | friction force of the piston seal at time = t |
| $P_c(t) - P_v(t)$ | = | differential pressure level which accelerates the piston at time = t |

Solution of the foregoing expression for lancet displacement (x) vs. time (t), from which lancet speed as a function of time can be determined, requires many auxiliary equations in the field of thermodynamics and compressible flow, which incorporate design details of the invention and the three-way valve. In general, the lancet speed ($U_p$) at the time of impact on the skin can be expressed in terms of the following variables:

$$U_p = F[A, M, S, X_p, K_s, X_s, C_v, Dt_v, V_c, V_v, P_a, P_v, T_a, Ff]$$

where

| | | |
|---|---|---|
| A | = | effective surface area of the piston on which air pressure acts |
| M | = | total inertial mass (piston + lancet assembly) |
| S | = | stroke distance of the piston |
| $X_p$ | = | lancet displacement when impact with skin occurs ($X_p < S$) |
| $K_s$ | = | spring rate constant of the return spring |
| $X_s$ | = | initial displacement of the return spring |
| $C_v$ | = | flow coefficient of the three-way valve when activated |
| $Dt_v$ | = | switching time of the three-way valve (time to fully activate) |
| $V_c$ | = | initial air volume between the piston and three-way valve |
| $V_v$ | = | initial cavity volume of the apparatus (i. e., measured volume of the cavity prior to actuation of the lancet) |
| $P_a$ | = | pressure level of the high-pressure air source |
| $P_v$ | = | initial pressure level of the cavity of the apparatus (i. e., measured pressure of low pressure air source prior to actuation of the lancet) |
| $T_a$ | = | air temperature level |
| Ff | = | friction force profile of the piston seal (typically varies as a function of the displacement of the piston) |

Maximizing the lancet speed within a specified stroke distance of the piston (S) is accomplished by selecting a three-way valve with high flow coefficient ($C_v$) and rapid switching time ($Dt_v$), by optimizing the surface area of the piston (A) and initial air volume between the piston and three-way valve ($V_c$), by minimizing the total inertial mass (M), the spring force ($K_s$, $X_s$), and the friction force profile of the piston seal (Ff), by ensuring adequate initial cavity volume ($V_v$), and by applying as much pressure differential ($P_a - P_v$) as permitted by the apparatus.

The lancing assembly that utilizes differential gas pressure offers several advantages over conventional lancing assemblies. The advantages are brought about by using differential gas pressure rather than a compressed spring to thrust the lancet into the skin. One advantage is that the lancet does not need to be manually cocked by the user before use. This simplifies usage and permits sequential lancing of the target skin to provide greater access to blood. Cocking is not required because the gas providing differential gas pressure is vented from the lancing assembly after use, thereby allowing the piston biasing means to force the lancet back to its original position. Another advantage is that the lancing assembly does not need to be mechanically triggered. This simplifies the design of the device and protects against accidental triggering by the user if the device is mishandled. A separate triggering mechanism is not required because the differential gas pressure functions to both initiate and execute the lancing process. Still another advantage is that the lancing assembly fully retracts the lancet when lancing is not in progress. This minimizes exposure of the user to the sharp lancet when handling the device in preparation for use or after use. Full retraction of the lancet is accomplished by the piston biasing means after the gas that provided the differential gas pressure has been vented from the lancing assembly.

The vacuum pump 14 is connected to the lancing assembly 16 by an evacuation tube 24. The air that is evacuated from the lancing assembly 16 by the vacuum pump 14 is removed via the evacuation tube 24. The evacuation tube 24 is typically made from a polymeric material. A check valve 26 is placed between the vacuum pump 14 and the lancing assembly 16 at a point in the evacuation tube 24 to prevent air removed from the lancing assembly 16 by the vacuum pump 14 from flowing back to the lancing assembly 16 and adversely affecting the vacuum.

A source of power for the vacuum pump 14 can be disposed within the housing 12. A source of power suitable for the device of this invention is a battery 18. Alternatively, an external source of power can be used to operate the vacuum pump 14. The power source is actuated by the electronics 20, which, in turn, is actuated by the switch 22.

The electronics 20 may incorporate a microprocessor or microcontroller. The function of the electronics 20 is to switch power on and off to operate the various components in the apparatus. These components include, but are not limited to, the vacuum pump 14. The electronics 20 can also be use to switch power on and off to operate components in alternative embodiments, e.g., heating elements, lancets, indicating devices, and valves. Electronics suitable for this invention is the "TATTLETALE MODEL 5 F" controller/data logger, commercially available from Onset Computer Corporation, 536 MacArthur Blvd. P.O. Box 3450, Pocasset, Mass. 02559-3450. Auxiliary electronic devices, such as power transistors, pressure monitors, and OP-Amps (operational amplifiers), may also be required in order to provide an interface between the controller and the operational components. All electronics required for this invention are well-known to one of ordinary skill in the art and are commercially available. Auxiliary electronic devices suitable for use in this invention include the following components:

| Component | Source | Catalog Number |
| --- | --- | --- |
| Mosfet Drivers | International Rectifier El Segundo, CA | IRLD024 |

-continued

| Component | Source | Catalog Number |
| --- | --- | --- |
| Op-Amp | National Semiconductor Santa Clara, CA | LM358 |
| Status LED | Hewlett-Packard Newark Electronics Schaumburg, IL | HLMPD150 |
| Pressure Sensor | Sensym, Inc. Milpitas, CA | SDX15D4 |

Figure 3:
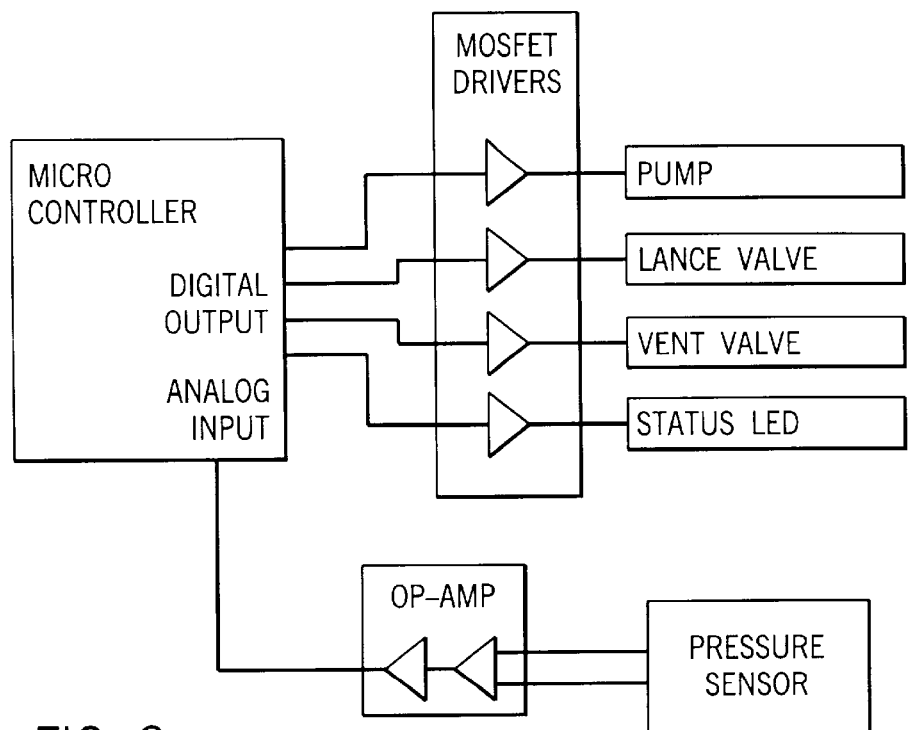
FIG. 3 is a block diagram illustrating the electronics of the preferred embodiment.

FIG. 3 illustrates by way of a block diagram how the foregoing electronic components can be arranged to carry out the method of the present invention.

Figure 2:
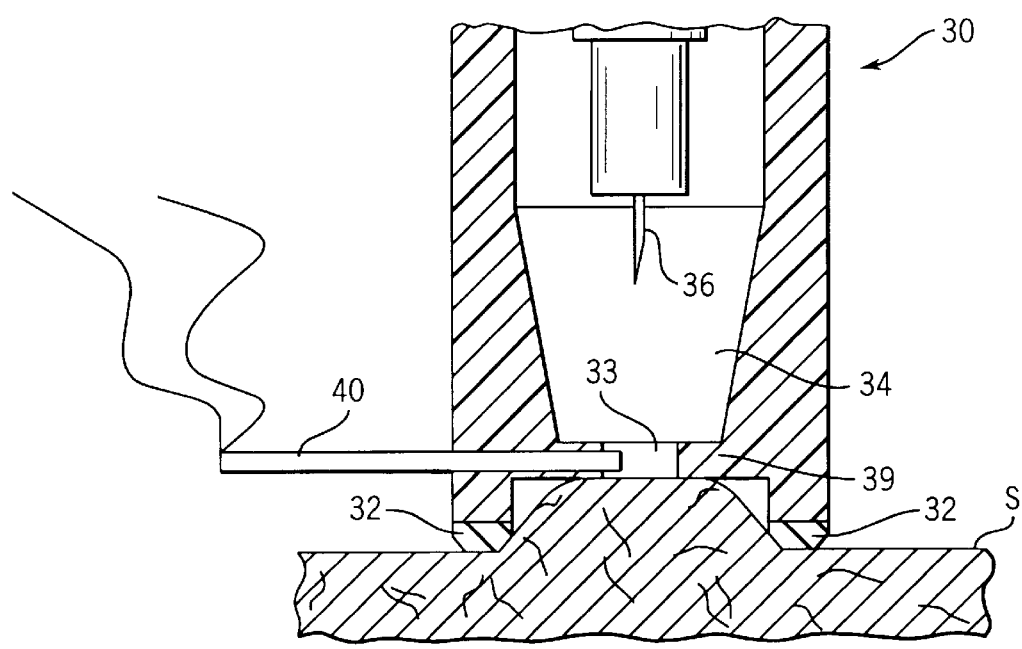
FIG. 2 is a schematic diagram illustrating how a vacuum causes a portion of the skin to become stretched prior to the formation of an opening in the skin from which the sample of blood is extracted.
Figure 4:
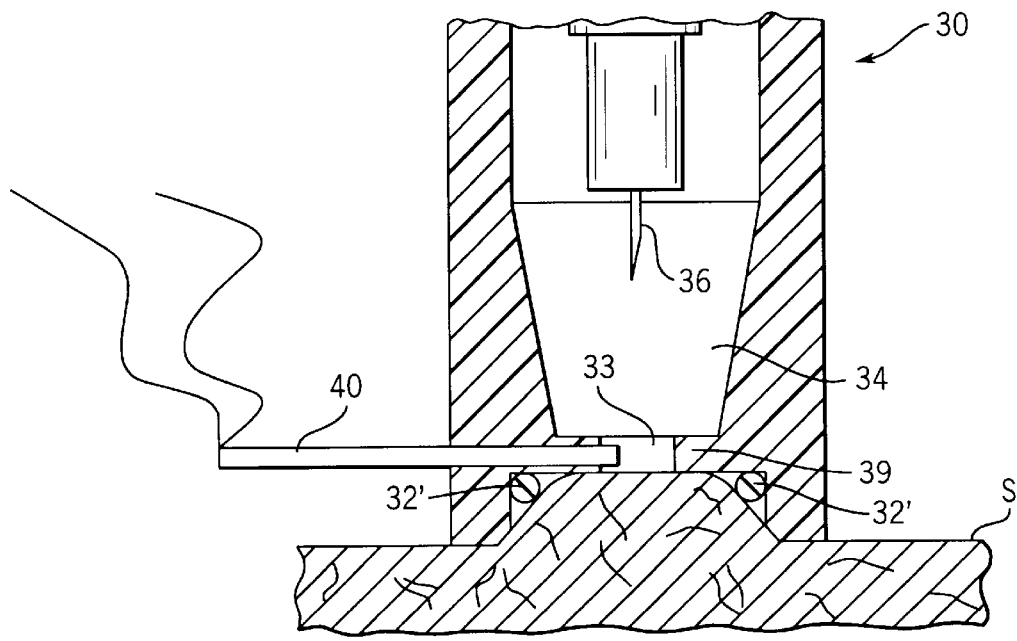
FIG. 4 is a schematic diagram illustrating an alternative seal for the vacuum of the device of the present invention.

Operation of the blood extraction device 10 will now be described. Referring now to FIGS. 1, 2 and 3, the nosepiece 30 of the lancing assembly 16 is applied to the surface of the skin, designated herein by the letter "S". The end of the nosepiece 30 that contacts the skin is equipped with a seal 32. The purpose of the seal 32 is to prevent air from leaking into blood extraction chamber 34, so that the vacuum pump 14 can provide sufficient suction action for increasing the availability of blood to the area of the skin from which the sample is to be extracted, stretching the skin, and extracting the sample of blood from the unobstructed opening in the skin. The seal 32 surrounds an opening 33 in the nosepiece 30. The opening 33 in the nosepiece allows communication between the surface of the skin and a blood extraction chamber 34 in the nosepiece 30. The seal 32 is preferably made of a rubber or an elastomeric material. FIG. 4 illustrates an alternative position for the seal 32. In FIG. 4, the seal is designated by the reference numeral 32'. The remaining parts of FIG. 4 are the same as those of FIG. 2, and, accordingly, retain the same reference numerals as were used in FIG. 2.

The switch 22 is actuated, typically by being pressed, thereby activating the electronics 20, which starts the vacuum pump 14. The vacuum pump 14 then provides a suction action. The suction action of the vacuum pump 14 causes the skin circumscribed by the seal 32 to become engorged with blood. Engorgement of the skin with blood is accompanied by a stretching of and rising up of the skin up to opening 33.

After an appropriate period of time, which is typically pre-set by the programmer of the electronics, the lancing assembly 16 is triggered, thereby causing the lancet 36 to penetrate the skin that has risen up to the opening 33 and that is engorged with blood. The lancet 36 is preferably triggered automatically, by a solenoid valve 38 that causes a vacuum-actuated piston (not shown) to trigger the lancet 36. The lancet 36 is then retracted, preferably automatically. Thereupon, the blood flows out of the unobstructed opening resulting from the lancet 36, and, aided by the vacuum generated by the vacuum pump 14, is collected. When sufficient blood has been collected or a pre-set time interval has passed, the electronics 20 causes the vacuum pump 14 to stop. The device 10 can then be removed from the surface of the skin after another solenoid valve (not shown because it is hidden under solenoid valve 38) is opened to vent the vacuum to allow ease of removal of the device from the surface of the skin. Solenoid valves suitable for use with the apparatus described herein are commercially available from The Lee Company, Essex, CT and have the part number LHDA0511111H.

Figure 15B:
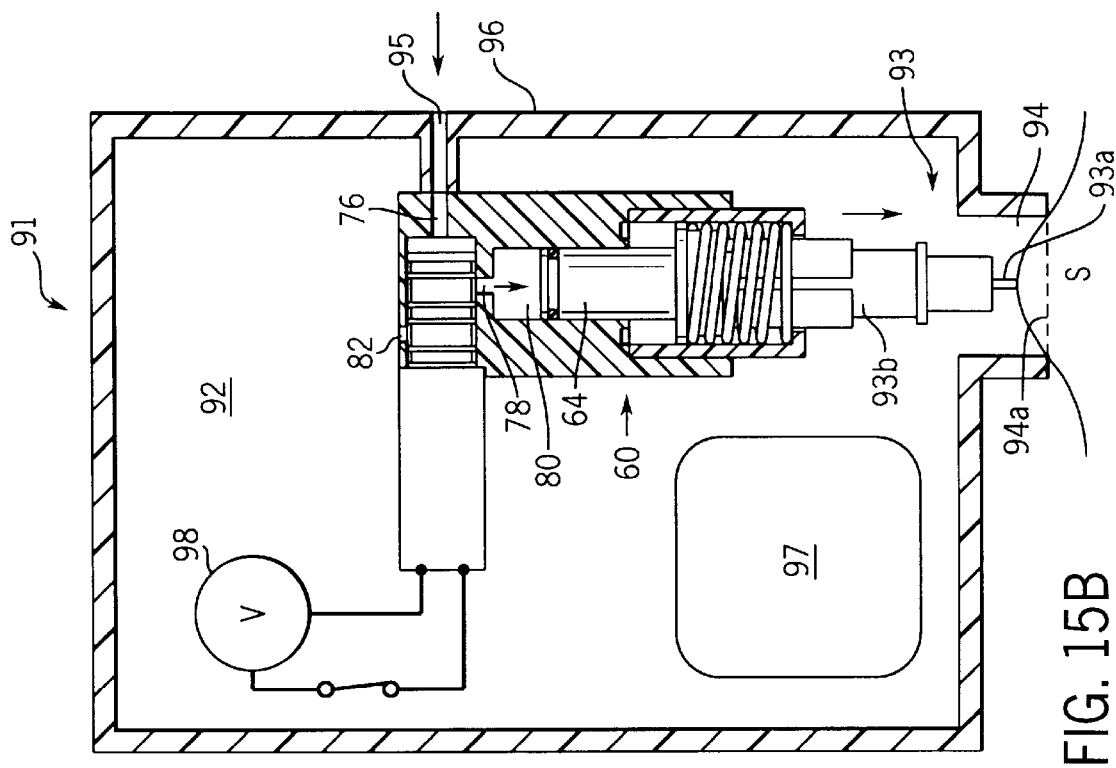
Figure 15A:
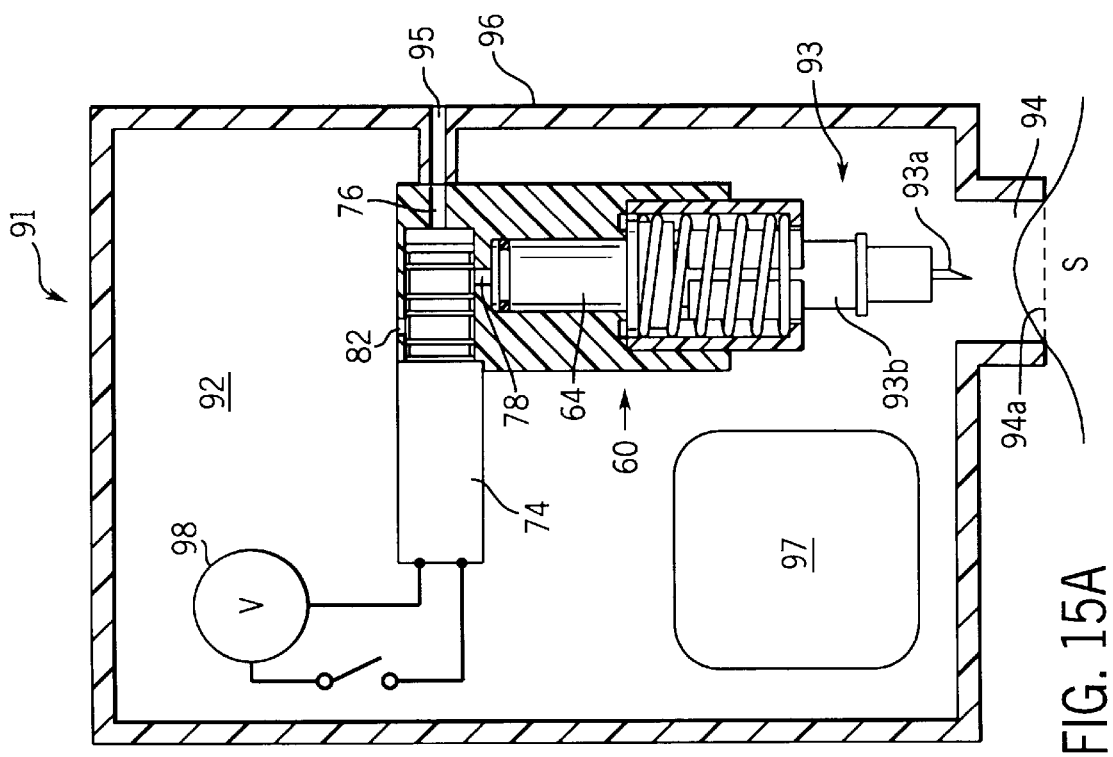

FIGS. 15A, 15B, and 15C illustrate an installation of the lancing assembly of FIGS. 11 and 12 inside a hypothetical apparatus 91. The lancing assembly 60 is fixed inside a cavity 92 of the apparatus 91 and fitted with a three-way solenoid valve 74 and a standard disposable lancet assembly 93 as shown. The lancet assembly 93 comprises a lancet 93a, which is inserted into a molded plastic body 93b. The apparatus 91 has a lower passage 94 through which the lancet assembly 93 can move to form an unobstructed opening in the area of the skin "S" that is circumscribed by a circular opening 94a (shown by dashed line) in the lower passage. A side port 95 on a wall 96 of the apparatus 91 connects inlet port 76 on the lancing assembly 60 to ambient air surrounding the apparatus 91. The apparatus 91 also has a vacuum source 97 to maintain the air pressure in the cavity 92 at the level at which the apparatus operates, and a voltage source 98 to selectively activate the three-way solenoid valve 74. With voltage off, the three-way solenoid valve 74 connects the bore 80 of the lancing assembly 60 with the cavity 92 via exit port 82, causing the piston 64 to experience no differential air pressure.

In the "Ready" mode (FIG. 15A), the lower passage 94 of the apparatus 91 is placed across the target skin. The vacuum pressure of the apparatus reaches operational level $P_v$, which is substantially less than ambient pressure $P_a$ (e.g., $P_v=-7.5$ psig, $P_a=0$ psig). The target skin is partially drawn into the lower passage 94 by vacuum pressure $P_v$. The voltage of the three-way solenoid valve 74 is initially off, thereby preventing ambient air from entering the lancing assembly 60, allowing the return spring 68 to maintain the lancet 93a at its maximum distance (e.g., 10 mm) from the skin.

In the "Lance" mode (FIG. 15B), the three-way solenoid valve 74 is activated by the voltage source 98, which allows ambient air to flow continuously through the side port 95 of the apparatus 91 through the inlet port 76 and then through the bore port 78 into the bore 80 of the lancing assembly 60. The flow of ambient air increases the air pressure in the bore 80, causing a differential air pressure to act on the piston 64. The differential air pressure acting on the piston 64 rapidly increases and overcomes the opposing force of the return spring 68 and the friction of the o-ring 84, causing the combined mass of the piston 64 and lancet assembly 93 (e.g., 1.5 grams) to thrust toward the target skin. The lancet 93a contacts the skin in a short period of time (e.g., 6 msec) and reaches sufficient speed (e.g., 3.5 m/sec) to form an opening in the skin and to penetrate to a specified depth (e.g., 1.5 mm). The opening in the skin is complete when the thrusting motion of the lancet assembly 93 is halted by some halting means. Suitable means for halting the lancet assembly 93 include, but are not limited to, the cap 70 within the lancing assembly 60, which, in effect, limits the stroke distance of the piston 64, and a lancet stop, as will be described in FIG. 20.

In the "Return" mode (FIG. 15C), the lancet 93a begins retracting from the skin when the voltage of the solenoid is shut off, which occurs after a predefined dwell time (e.g., 10 msec). With voltage off, the three-way solenoid valve 74 reconnects the bore 80 to exit port 82 in the lancing assembly 60 via the bore port 78, causing air from the bore 80 to vent quickly (e.g., 15 msec) through the three-way solenoid valve 74 and out through exit port 82 into the cavity 92, which contains low-pressure air, provided in the apparatus by the vacuum source 97. During venting, the compressed return spring 68 overcomes the combined force of the differential air pressure and the friction of the o-ring 84 to move the piston 64 and the lancet assembly 93 back to the starting position. The lancing cycle, which requires a total of 25 msec in this hypothetical apparatus, is then complete.

The solenoid is driven by the voltage system of the apparatus. Each time the voltage is turned on and then turned off (i.e., one pulse), the three-way solenoid valve 74 switches internally, first directing flow of air into the lancing assembly 60 and then away from the lancing assembly 60. This switching causes the lancet to be thrust into the target skin tissue, then to be retracted away from the target skin tissue. By pulsing the solenoid repeatedly with voltage, the lancing process is repeated. This feature has been termed "repetitive lancing."

The resulting opening formed in the skin is similar to that achieved with conventional lancing devices; such an opening is capable of allowing a volume of biological fluid (e.g., 3 $\mu$L capillary blood) to be sampled for analysis.

The lancing process illustrated in FIGS. 15A, 15B, 15C can be repeated as many times as desired using the same lancet and without disturbing the device or target skin. With the skin still held in place by vacuum suction, the solenoid voltage can be pulsed as needed to lance the target area more than one time. Repetitive lancing has two potential benefits. First, it can be coordinated with an indexing system in the apparatus to lance a matrix of sites on the target skin for additional access to biological fluid. Second, it can increase the lancing success rate at or near a single site, by sequentially lancing into the skin until the desired amount of blood is obtained.

The blood is preferably directly collected on the application zone of a glucose detector, e.g., a reflectance strip or biosensor. The blood can then be used as the sample for a determination of glucose concentration in blood. Alternatively, the blood can be collected by other collection devices, such as, for example, a capillary tube or absorbent paper.

The apparatus of the present invention can include a glucose detector for analyzing the blood sample extracted by the apparatus. Glucose detectors are well-known in the art. With respect to glucose monitoring, there are two major categories of glucose detectors—reflectometers and biosensors. Representative examples of reflectometers suitable for this invention are described in U.S. Pat. No. 4,627,445, incorporated herein by reference. Representative examples of biosensors suitable for this invention are described in U.S. Pat. No. 5,509,410, incorporated herein by reference.

The glucose detector is preferably disposed in the nosepiece 30 of the lancing assembly 16. The glucose detector must be located at a position sufficiently close to the site of blood extraction so that the quantity of extracted blood collected will be sufficient to carry out a standard glucose monitoring test. Typically, this distance will preferably be no more than 5 mm from the site of blood extraction, more preferably no more than 3 mm from the site of blood extraction, most preferably no more than 1 mm from the site of blood extraction. Care must be taken in the placement of the glucose detector so that the detector does not adversely affect the vacuum, when a vacuum is employed to aid in the extraction of blood. In addition, the glucose detector 40 should be modified, if necessary, so that the blood collected in the collection zone of the glucose detector is capable of being used to activate the glucose detector.

FIG. 2 also illustrates a manner for disposing a glucose detector 40 in the nosepiece 30 of the lancing assembly 16.

Figure 5:
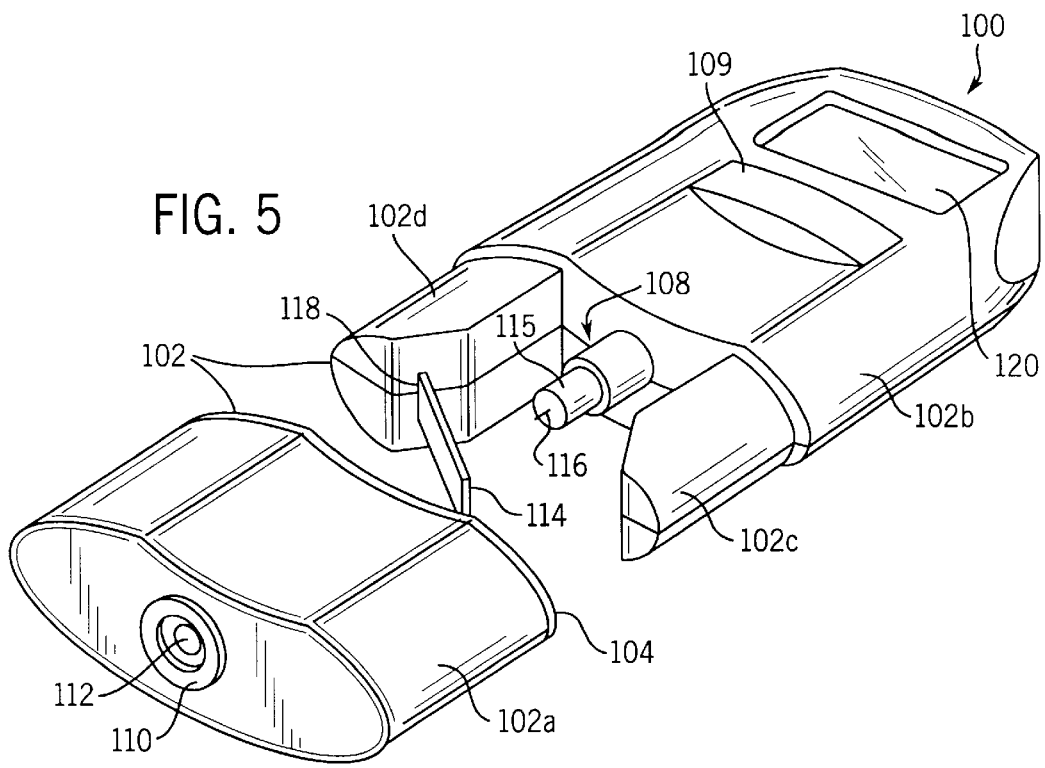
FIG. 5 is a perspective view of an embodiment of the apparatus of this invention. In this figure, the housing of the apparatus is open.

FIGS. 5, 6, 7, 8, 9, and 10 illustrate various alternative embodiments of the apparatus of this invention. In FIG. 5, blood extraction device 100 comprises a housing 102. The housing 102 is separable into two portions, a receiving portion 102a and a projecting portion 102b. A gasket 104 is provided to seal the portions 102a and 102b of the housing 102 and to aid in separation of the receiving portion 102a from the projecting portion 102b. The receiving portion 102a forms a tight fit with the projecting portion 102b by means of friction. Projecting elements 102c and 102d are used to guide the projecting portion 102b into the receiving portion 102a. Disposed within the housing 102 are a vacuum pump (not shown), a lancing assembly 108, a battery (not shown), and electronics (not shown). A switch 109 is provided to activate the electronics. The vacuum pump is connected to the lancing assembly 108 by an evacuation tube (not shown). A check valve (not shown) is placed between the vacuum pump and the lancing assembly 108.

During the process of obtaining the sample, the receiving portion 102a and the projecting portion 102b are fitted tightly together. The area of the receiving portion 102a of the housing 102 of the device 100 that is to contact the skin is equipped with a seal 110. The seal 110 surrounds an opening 112 in the receiving portion 102a. The opening 112 in the receiving portion 102a allows communication between the surface of the skin and a blood extraction chamber adjacent to a glucose detector 114, shown here in the shape of a strip. When in use, the device 100 is positioned so that the lancing assembly 108 is placed over the region on the surface of the skin from which the sample is to be obtained. In order to obtain the sample of blood, the receiving portion 102a of the housing 102 of the device 100 is placed against the skin, whereby the seal 110 allows a satisfactory vacuum to be effected. The switch 109 is actuated, typically by being pressed, thereby activating the electronics, which starts the vacuum pump. The vacuum pump then provides a suction action. The suction action of the vacuum pump causes the skin circumscribed by the seal 110 to become engorged with blood. Engorgement of the skin with blood is accompanied by a stretching of and rising up of the skin up to the opening 112. After an appropriate period of time, which is typically pre-set by the programmer of the electronics, the lancing assembly 108 is triggered, thereby causing the lancet 116 to penetrate the skin that has risen up to the opening 112 and that is engorged with blood. The lancet 116 is preferably triggered automatically, by a solenoid valve (not shown) that causes a vacuum-actuated piston (not shown) to trigger the lancet 116. The remaining steps of the process relating to collection of a sample of blood are substantially similar to the steps described in the embodiment shown in FIGS. 1, 2, 3, and 4.

In the embodiment shown in FIG. 5, the glucose detector 114 is inserted into a slot 118 in the projecting portion 102b of the housing 102. The receiving portion 102a of the housing 102 causes the glucose detector 114 to be moved into its proper position for testing. The results obtained from the glucose detector 114 can be displayed on a screen 120, typically a conventional liquid crystal digital display. The receiving portion 102a is separated from the projecting portion 102b when the lancet 116 or glucose detector 114 is being replaced. The receiving portion 102a is fitted tightly to the projecting portion 102b during the process of obtaining a sample of blood.

Figure 6:
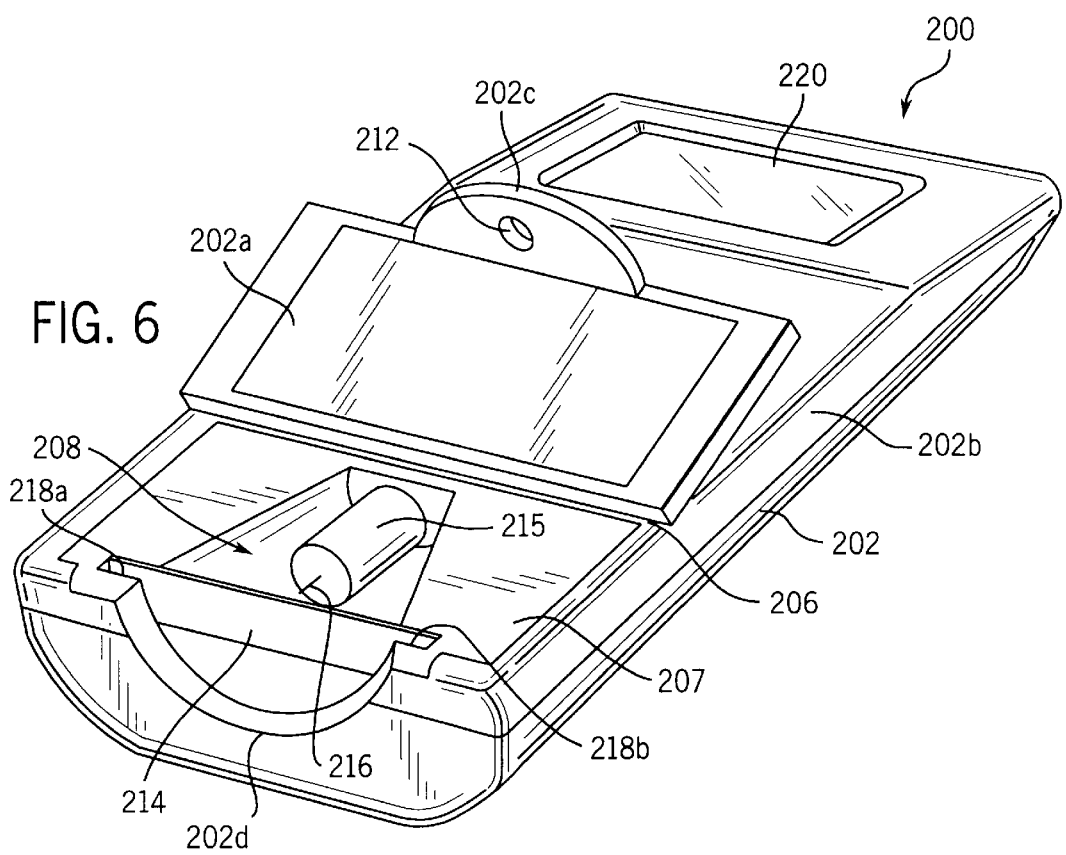
FIG. 6 is a perspective view of an embodiment of the apparatus of this invention. In this figure, the housing of the apparatus is open.

The relative positions of the vacuum pump, the battery, the electronics, the evacuation tube, the check valve, the solenoid valves, and the vacuum-actuated piston are substantially similar to the relative positions of these components as described in the embodiments shown in FIGS. 1 and 2. In FIG. 6, blood extraction device 200 comprises a housing 202. The housing 202 comprises a door portion 202a that is attached to the remaining portion 202b of the housing 202 by a hinge 206. A gasket 207 is provided to seal the housing 202 when the door portion 202a is closed. The door portion 202a can be closed by pivoting it around the hinge 206. When the door portion 202a is closed, the convex portion 202c of the door portion 202a fits precisely into the concave portion 202d of the remaining portion 202b of the housing 202. The remaining edges of the door portion 202a fit tightly against the remaining edges of the remaining portion 202b of the housing 202. Disposed within the housing 202 are a vacuum pump (not shown), a lancing assembly 208, a battery (not shown), and electronics (not shown). A switch (not shown) is provided to activate the electronics. The vacuum pump is connected to the lancing assembly 208 by an evacuation tube (not shown). A check valve (not shown) is placed between the vacuum pump and the lancing assembly 208.

During the process of obtaining the sample, the door portion 202a is closed. The area of the door portion 202a of the housing 202 of the device 200 that is to contact the skin is equipped with a seal (not shown). The seal surrounds an opening 212 in the door portion 202a. The opening 212 in the door portion 202a allows communication between the surface of the skin and a blood extraction chamber adjacent to a glucose detector 214, shown here in the shape of a strip. When in use, the device 200 is positioned so that the lancing assembly 208 is placed over the region on the surface of the skin from which the sample is to be obtained. In order to obtain the sample of blood, the door portion 202a of the housing 202 of the device 200 is placed against the skin, whereby the seal allows a satisfactory vacuum to be effected. The switch is actuated, typically by being pressed, thereby activating the electronics, which starts the vacuum pump. The vacuum pump then provides a suction action. The suction action of the vacuum pump causes the skin circumscribed by the seal to become engorged with blood. Engorgement of the skin with blood is accompanied by a stretching of and rising up of the skin up to the opening 212. After an appropriate period of time, which is typically pre-set by the programmer of the electronics, the lancing assembly 208 is triggered, thereby causing the lancet 216 to penetrate the skin that has risen up to the opening 212 and that is engorged with blood. The lancet 216 is preferably triggered automatically, by a solenoid valve (not shown) that causes a vacuum-actuated piston (not shown) to trigger the lancet 216. The remaining steps of the process relating to collection of a sample of blood are substantially similar to the steps described in the embodiment shown in FIGS. 1, 2, 3, and 4.

In the embodiment shown in FIG. 6, the glucose detector 214 is inserted into slots 218a and 218b of the housing 202. The results obtained from the glucose detector 214 can be displayed on screen 220, typically a conventional liquid crystal digital display. The door portion 202a is opened when the lancet 216 or glucose detector 214 is being replaced. The door portion 202a is closed during the process of obtaining a sample of blood.

The relative positions of the vacuum pump, the battery, the electronics, the switch, the evacuation tube, the check valve, the seal, the solenoid valves, and the vacuum-actuated piston are substantially similar to the relative positions of these components as described in the embodiments shown in FIGS. 1 and 2.

Figure 7:
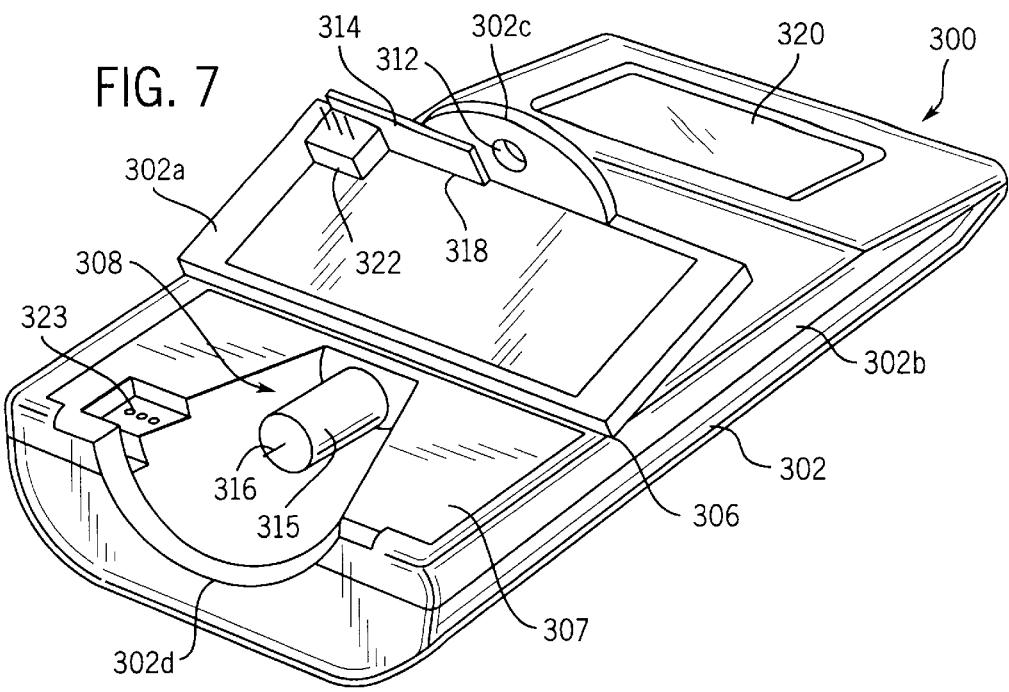
FIG. 7 is a perspective view of an embodiment of the apparatus of this invention. In this figure, the housing of the apparatus is open.

In FIG. 7, blood extraction device 300 comprises a housing 302. The housing 302 comprises a door portion 302a that is attached to the remaining portion 302b of the housing 302 by a hinge 306. A gasket 307 is provided to seal the housing 302 when the door portion 302a is closed. The door portion 302a can be closed by pivoting it around the hinge 306. When the door portion 302a is closed, the convex portion 302c of the door portion 302a fits precisely into the concave portion 302d of the remaining portion 302b of the housing 302. The remaining edges of the door portion 302a fit tightly against the remaining edges of the remaining portion 302b of the housing 302. Disposed within the housing 302 are a vacuum pump (not shown), a lancing assembly 308, a battery (not shown), and electronics (not shown). A switch (not shown) is provided to activate the electronics. The vacuum pump is connected to the lancing assembly 308 by an evacuation tube (not shown). A check valve (not shown) is placed between the vacuum pump and the lancing assembly 308.

During the process of obtaining the sample, the door portion 302a is closed. The area of the door portion 302a of the housing 302 of the device 300 that is to contact the skin is equipped with a seal (not shown). The seal surrounds an opening 312 in the door portion 302a. The opening 312 in the door portion 302a allows communication between the surface of the skin and a blood extraction chamber adjacent to a glucose detector 314, shown here in the shape of a strip. When in use, the device 300 is positioned so that the lancing assembly 308 is placed over the region on the surface of the skin from which the sample is to be obtained. In order to obtain the sample of blood, the door portion 302a of the housing 302 of the device 300 is placed against the skin, whereby the seal allows a satisfactory vacuum to be effected. The switch is actuated, typically by being pressed, thereby activating the electronics, which starts the vacuum pump. The vacuum pump then provides a suction action. The suction action of the vacuum pump causes the skin circumscribed by the seal to become engorged with blood. Engorgement of the skin with blood is accompanied by a stretching of and rising up of the skin up to the opening 312. After an appropriate period of time, which is typically pre-set by the programmer of the electronics, the lancing assembly 308 is triggered, thereby causing the lancet 316 to penetrate the skin that has risen up to the opening 312 and that is engorged with blood. The lancet 316 is preferably triggered automatically, by a solenoid valve (not shown) that causes a vacuum-actuated piston (not shown) to trigger the lancet 316. The remaining steps of the process relating to collection of a sample of blood are substantially similar to the steps described in the embodiment shown in FIGS. 1, 2, 3, and 4.

In the embodiment shown in FIG. 7, the glucose detector 314 is inserted into a slot 318 of the housing 302. The results obtained from the glucose detector 314 can be displayed on screen 320, typically a conventional liquid crystal digital display. In FIG. 7, connections 322 for the electronics are shown. The door portion 302a is opened when the lancet 316 or glucose detector 314 is being replaced. The door portion 302a is closed during the process of obtaining a sample of blood.

The relative positions of the vacuum pump, the battery, the electronics, the switch, the evacuation tube, the check valve, the seal, the solenoid valves, and the vacuum-actuated piston are substantially similar to the relative positions of these components as described in the embodiments shown in FIGS. 1 and 2.

Figure 8:
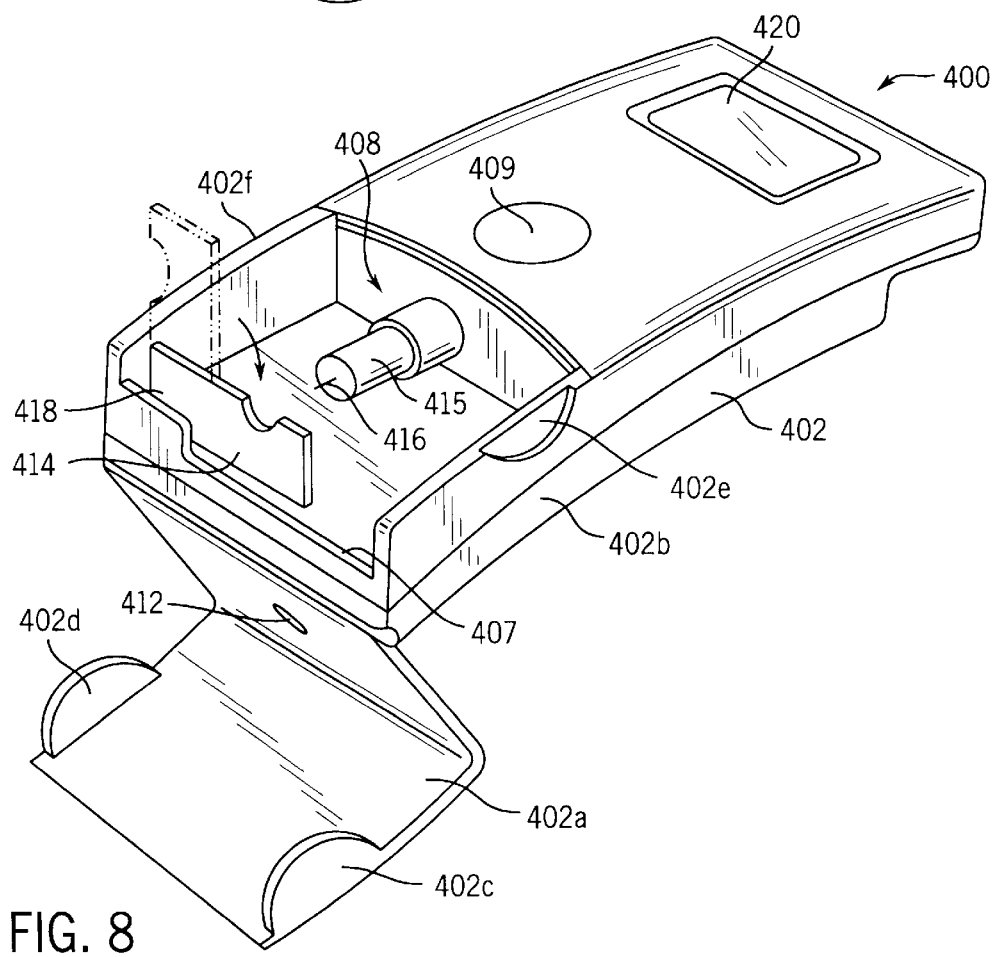
FIG. 8 is a perspective view of an embodiment of the apparatus of this invention. In this figure, the housing of the apparatus is open.
Figure 14:
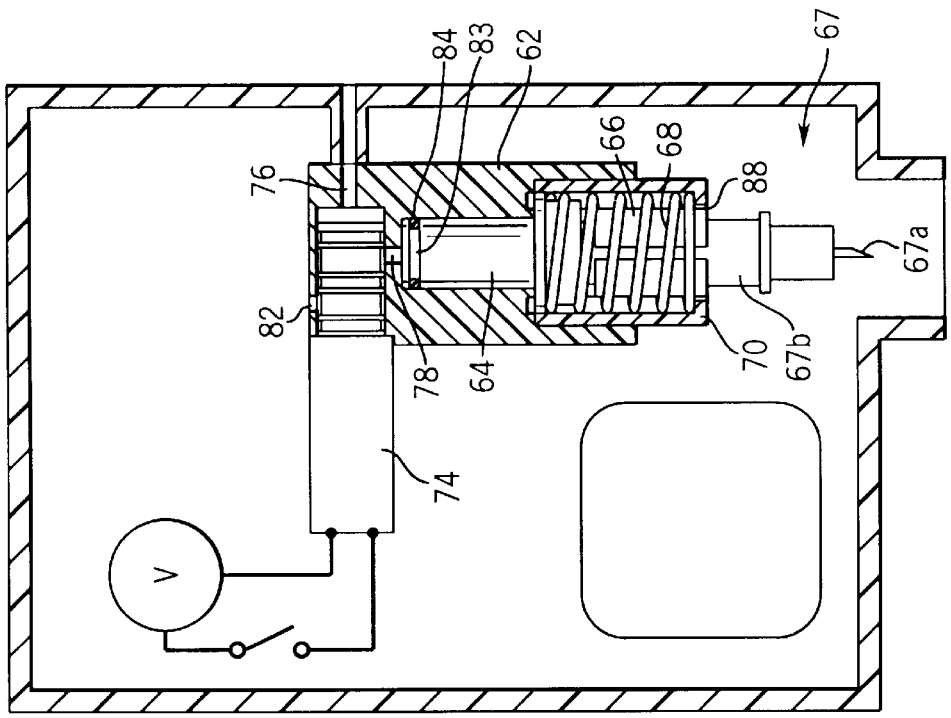
FIG. 14 is a schematic diagram illustrating the positioning of the components of the lancing assembly of this invention. In this figure, the lancet has been inserted into the lancet holder and the valve has been inserted into the valve manifold.
Figure 13:
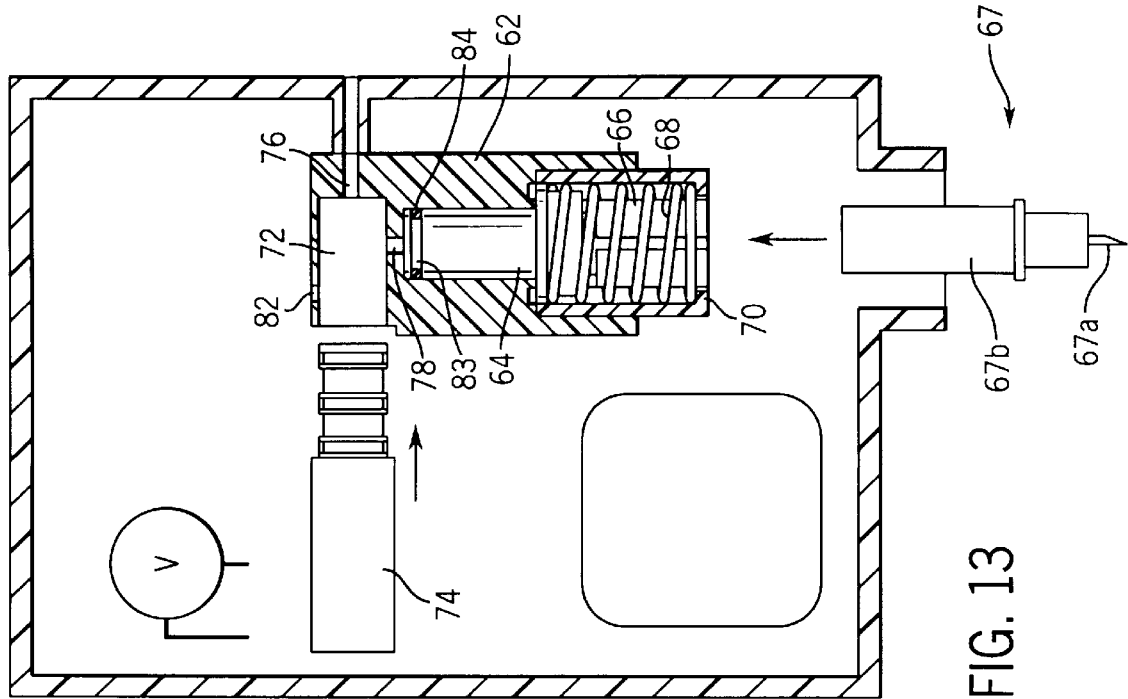
FIG. 13 is a schematic diagram illustrating the positioning of the components of the lancing assembly of this invention. In this figure, the lancet assembly has not yet been inserted into the lancet holder and the valve has not yet been inserted into the valve manifold.

In FIG. 8, blood extraction device 400 comprises a housing 402. The housing 402 comprises a door portion 402a that is attached to the remaining portion 402b of the housing 402 by a hinge 406. A gasket 407 is provided to seal the housing 402 when the door portion 402a is closed. The door portion 402a can be closed by pivoting it around the hinge 406. When the door portion 402a is closed, the convex portions 402c and 402d of the door portion 402a fit precisely into the concave portions 402e and 402f, respectively, of the remaining portion 402b of the housing 402. The remaining edges of the door portion 402a fit tightly against the remaining edges of the remaining portion 402b of the housing 402. Disposed within the housing 402 are a vacuum pump (not shown), a lancing assembly 408, a battery (not shown), and electronics (not shown). A switch 409 is provided to activate the electronics. The vacuum pump is connected to the lancing assembly 408 by an evacuation tube (not shown). A check valve (not shown) is placed between the vacuum pump and the lancing assembly 408.

During the process of obtaining the sample, the door portion 402a is closed. The area of the door portion 402a of the housing 402 of the device 400 that is to contact the skin is equipped with a seal (not shown). The seal surrounds an opening 412 in the door portion 402a. The opening 412 in the door portion 402a allows communication between the surface of the skin and a blood extraction chamber adjacent to a glucose detector 414, shown here in the shape of a strip. When in use, the device 400 is positioned so that the lancing assembly 408 is placed over the region on the surface of the skin from which the sample is to be obtained. In order to obtain the sample of blood, the door portion 402a of the housing 402 of the device 400 is placed against the skin, whereby the seal allows a satisfactory vacuum to be effected. The switch 409 is actuated, typically by being pressed, thereby activating the electronics, which starts the vacuum pump. The vacuum pump then provides a suction action. The suction action of the vacuum pump causes the skin circumscribed by the seal to become engorged with blood. Engorgement of the skin with blood is accompanied by a stretching of and rising up of the skin up to the opening 412. After an appropriate period of time, which is typically pre-set by the programmer of the electronics, the lancing assembly 408 is triggered, thereby causing the lancet 416 to penetrate the skin that has risen up to the opening 412 and that is engorged with blood. The lancet 416 is preferably triggered automatically, by a solenoid valve (not shown) that causes a vacuum-actuated piston (not shown) to trigger the lancet 416. The remaining steps of the process relating to collection of a sample of blood are substantially similar to the steps described in the embodiment shown in FIGS. 1, 2, 3, and 4.

In the embodiment shown in FIG. 8, the glucose detector 414 is inserted into a slot 418 of the housing 402. In this embodiment, it is shown that glucose detector 14 can be rotated 90° between two positions to simplify insertion and replacement thereof. The results obtained from the glucose detector 414 can be displayed on screen 420, typically a conventional liquid crystal digital display. The door portion 402a is opened when the lancet 416 or glucose detector 414 is being replaced. The door portion 402a is closed during the process of obtaining a sample of blood.

The relative positions of the vacuum pump, the battery, the electronics, the evacuation tube, the check valve, the seal, the solenoid valves, and the vacuum-actuated piston are substantially similar to the relative positions of these components as described in the embodiments shown in FIGS. 1 and 2.

In FIG. 9, blood extraction device 500 comprises a housing 502. The housing 502 comprises a cover portion 502a that is attached to the remaining portion 502b of the housing 502 by a hinge 506. A gasket 507 is provided to seal the housing 502 when the cover portion 502a is closed. The cover portion 502a can be closed by pivoting it around the hinge 506. When the cover portion 502a is closed, edges 502c of the cover portion 502a tightly fit against edges 502d of the remaining portion 502b of the housing 502. Disposed within the housing 502 are a vacuum pump (not shown), a lancing assembly 508, a battery (not shown), and electronics (not shown). A switch (not shown) is provided to activate the electronics. The vacuum pump is connected to the lancing assembly 508 by an evacuation tube (not shown). A check valve (not shown) is placed between the vacuum pump and the lancing assembly 508.

During the process of obtaining the sample, the cover portion 502a is closed. The cover portion 502a of the housing 502 of the device 500 that is to contact the skin is equipped with a seal 511. The seal 511 surrounds an opening 512 in the cover portion 502a. The opening 512 in the cover portion 502a allows communication between the surface of the skin and a blood extraction chamber adjacent to a glucose detector 514, shown here in the shape of a strip. When in use, the device 500 is positioned so that the lancing assembly 508 is placed over the region on the surface of the skin from which the sample is to be obtained. In order to obtain the sample of blood, the cover portion 502a of the housing 502 of the device 500 is placed against the skin, whereby the seal allows a satisfactory vacuum to be effected. The switch is actuated, typically by being pressed, thereby activating the electronics, which starts the vacuum pump. The vacuum pump then provides a suction action. The suction action of the vacuum pump causes the skin circumscribed by the seal to become engorged with blood. Engorgement of the skin with blood is accompanied by a stretching of and rising up of the skin up to the opening 512. After an appropriate period of time, which is typically pre-set by the programmer of the electronics, the lancing assembly 508 is triggered, thereby causing the lancet 516 to penetrate the skin that has risen up to the opening 512 and that is engorged with blood. The lancet 516 is preferably triggered automatically, by a solenoid valve (not shown) that causes a vacuum-actuated piston (not shown) to trigger the lancet 516. The remaining steps of the process relating to collection of a sample of blood are substantially similar to the steps described in the embodiment shown in FIGS. 1, 2, 3, and 4.

In the embodiment shown in FIG. 9, the glucose detector 514 is inserted into a slot 518 of the housing 502. The results obtained from the glucose detector 514 can be displayed on screen 520, typically a conventional liquid crystal digital display. The cover portion 502a is opened when the lancet 516 or glucose detector 514 is being replaced. The cover portion 502a is closed during the process of obtaining a sample of blood.

The relative positions of the vacuum pump, the battery, the electronics, the switch, the evacuation tube, the check valve, the solenoid valves, and the vacuum-actuated piston are substantially similar to the relative positions of these components as described in the embodiments shown in FIGS. 1 and 2.

In FIG. 10, blood extraction device 600 comprises a housing 602. The housing 602 comprises a cover portion 602a that is attached to the remaining portion 602b of the housing 602 by a hinge 606. A gasket 607 is provided to seal the housing 602 when the cover portion 602a is closed. The cover portion 602a can be closed by pivoting it around the hinge 606. When the cover portion 602a is closed, edges 602c of the cover portion 602a tightly fit against edges 602d of the remaining portion 602b of the housing 602. Disposed within the housing 602 are a vacuum pump (not shown), a lancing assembly 608, a battery (not shown), and electronics (not shown). A switch 609 is provided to activate the electronics. The vacuum pump is connected to the lancing assembly 608 by an evacuation tube (not shown). A check valve (not shown) is placed between the vacuum pump and the lancing assembly 608.

During the process of obtaining the sample, the cover portion 602a is closed. The cover portion 602a of the housing 602 of the device 600 that contacts the skin is equipped with a seal 611. The seal 611 surrounds an opening 612 in the cover portion 602a. The opening 612 in the cover portion 602a allows communication between the surface of the skin and a blood extraction chamber adjacent to a glucose detector 614, shown here in the shape of a strip. When in use, the device 600 is positioned so that the lancing assembly 608 is placed over the region on the surface of the skin from which the sample is to be obtained. In order to obtain the sample of blood, the cover portion 602a of the housing 602 of the device 600 is placed against the skin, whereby the seal allows a satisfactory vacuum to be effected. The switch is actuated, typically by being pressed, thereby activating the electronics, which starts the vacuum pump. The vacuum pump then provides a suction action. The suction action of the vacuum pump causes the skin circumscribed by the seal to become engorged with blood. Engorgement of the skin with blood is accompanied by a stretching of and rising up of the skin up to the opening 612. After an appropriate period of time, which is typically pre-set by the programmer of the electronics, the lancing assembly 608 is triggered, thereby causing the lancet 616 to penetrate the skin that has risen up to the opening 612 and that is engorged with blood. The lancet 616 is preferably triggered automatically, by a solenoid valve (not shown) that causes a vacuum-actuated piston (not shown) to trigger the lancet 616. The remaining steps of the process relating to collection of a sample of blood are substantially similar to the steps described in the embodiment shown in FIGS. 1, 2, 3, and 4.

In the embodiment shown in FIG. 10, the glucose detector 614 is inserted into a slot 618 of the housing 602. The results obtained from the glucose detector 614 can be displayed on screen 620, typically a conventional liquid crystal digital display. The cover portion 602a is opened when the lancet 616 or glucose detector 614 is being replaced. The cover portion 602a is closed during the process of obtaining a sample of blood.

The relative positions of the vacuum pump, the battery, the electronics, the switch, the evacuation tube, the check valve, the solenoid valves, and the vacuum-actuated piston are substantially similar to the relative positions of these components as described in the embodiments shown in FIGS. 1 and 2.

In each of the embodiments shown in the foregoing FIGS. 5, 6, 7, 8, 9, and 10, the housing, vacuum pump, lancing assembly, battery, electronics, evacuation tube, check valve, nosepiece, seal, opening, blood extraction chamber, lancet, and solenoid valve can be made of the same materials as the corresponding components of the apparatus shown in FIGS. 1, 2, and 3. The gaskets 104, 207, 307, 407, 507, and 607 can be made of the same material as the seal. The components shown in the foregoing FIGS. 5, 6, 7, 8, 9, and 10 function in the same manner as do the corresponding components of the apparatus shown in FIGS. 1, 2, and 3.

It should be noted that the designs of the various housings shown in FIGS. 5, 6, 7, 8, 9, and 10 can be modified without substantially affecting the functioning of the components disposed within the housing or on the surface of the housing. For example, the shapes of the housings, the shapes of the door portions of the housings, the shapes of the cover portions of the housings, and the shapes of the remaining portions of the housings can be modified without departing from the scope and spirit of this invention.

This invention provides numerous advantages over blood extraction devices of the prior art. Among these advantages are the following:

1. Ability to use parts of the body, other than the finger, as a site for the extraction of blood;
2. Reduction of pain by eliminating the need to lance the finger;
3. Increase in speed of collection of blood samples by means of pre-treatment comprising a combination of stretching of the skin in conjunction with heat or vacuum or both heat and vacuum;
4. Incorporation of glucose detector in apparatus for extracting the blood sample.

The following examples illustrate various features of the present invention but is not intended to in any way limit the scope of the invention as set forth in the claims. In the following examples, the term "pierce" and forms thereof and the term "puncture" and forms thereof are used interchangeably. Although the expression "glucose detector" is used herein, one of ordinary skill in the art will recognize that the apparatus and methods of the present invention can also be used to perform other diagnostic tests.

Pain of 1=person did not feel anything or not sure if anything was felt

Pain of 2=person felt definite prick, not as painful as piercing of finger by standard finger lancet Pain of 3=person felt definite pain, approximately equal to a piercing of finger by standard finger lancet Blood collection results are set forth in TABLE I.

TABLE I

| Frequency (hertz) | Average volume of blood sample collected at −2.5 psig ($\mu$L) | Percent of samples having >1 $\mu$L of blood collected at −2.5 psig | Average volume of blood sample collected at −5.0 psig ($\mu$L) | Percent of samples having >1 $\mu$L of blood collected at −5.0 psig |
|---|---|---|---|---|
| 0 (Continuous) | 1.6 | 69 | 3.1 | 94 |
| 0.2 | 1.1 | 44 | 3.0 | 94 |
| 0.8 | 1.1 | 63 | | 75 |
| 3.2 | 1.5 | 56 | 3.8 | 75 |
| 12.5 | 1.8 | 75 | 3.1 | 100 |
| 25 | 2.3 | 75 | 3.2 | 94 |
| 100 | 2.4 | 81 | 2.7 | 88 |

With no vacuum, average volume of blood collected was 0.8 $\mu$L and 31% of the samples collected contained more than 1 $\mu$L. The pain results were as follows:

pain of 1=81% pain of 2=17% pain of 3=2%

The control runs (no vacuum) provided much lower volumes of blood collected than did the runs where vacuum was applied. Increased vacuum resulted in higher volumes of blood extracted. The pain was minimal, with only 2% of the punctures resulting in pain comparable to that resulting from a piercing of the finger.

EXAMPLES

Example 1

This example illustrates that greater volumes of blood can be extracted and collected by applying a vacuum, pulsed or continuous, after piercing than can be extracted and collected when no vacuum is applied. No vacuum was applied prior to piercing.

Each of four people had his forearm (dorsal forearm) punctured four times (at four different positions on the forearm) with a "BD ULTRA-FINE" lancet in a "MEDIS-ENSE" lancet assembly (Model no. 97101) at two different levels of vacuum (−2.5 psig and −5.0 psig) and for each different vacuum pulsing frequencies (0, 0.2, 0.8, 3.2, 12.8, 25, 100 hertz). The vacuum was applied with a pipette tip having a diameter of 8 mm ("RAININ RT-200"). Four control runs without a vacuum were also carried out (one puncture per person). A total of 60 punctures per person were carried out. Accordingly, it can be seen that a total of 240 runs were carried out.

The vacuum was applied for a duration of 30 seconds after puncturing. Blood was collected into capillary tubes. In the control runs, the samples were extracted and collected 30 seconds after puncturing. The amount of blood collected was determined by measuring the length of blood in the tubes. The percentage of collections in which the volume of blood collected exceeded 1.0 $\mu$L was calculated. Sensation of pain was also recorded. The following pain scores were used:

Example 2

This example illustrates that application of vacuum prior to piercing as well as after piercing results in a greater volume of blood extracted than does the application of vacuum only after piercing.

Each of four people had his forearm (dorsal forearm, middle of forearm) punctured sixteen times (at sixteen different positions on the forearm) with a "BD ULTRA-FINE" lancet in a modified "MEDISENSE" lancet assembly at four different levels of vacuum. The four levels of vacuum used were −2.5, −5.0, −7.5, and −10.0 psig. The "MEDISENSE" lancet device was modified to allow vacuum to be pulled through the lancet assembly. Four punctures per person were carried out at each of the four levels of continuous vacuum. Accordingly, it can be seen that a total of 64 runs were carried out.

Prior to puncturing, the vacuum was applied for a period of 30 seconds; subsequent to puncturing, the vacuum was applied for a period of 30 seconds. The skin was under vacuum at the time the lancet was triggered. After the lancet was triggered, the lancet assembly was removed, and the vacuum was used to apply the same level of vacuum that had been used for the vacuum prior to puncturing. The vacuum, both prior to puncturing and subsequent to puncturing, was applied with a pipette tip having a diameter of 8 mm ("RAININ RT-200"). The pipette tip of the vacuum device was held level to the plane of the skin. Blood was then collected into capillary tubes. The amount of blood collected was determined by measuring the length of blood in the tubes. The percentage of collections in which the volume of blood collected exceeded 1.0 µL was calculated. Sensation of pain was also recorded. Blood collection results are set forth in TABLE II.

TABLE II

| Vacuum level (psig) | Average volume of blood sample collected (µL) | Percent of samples having >1 µL of blood collected |
|---|---|---|
| −2.5 | 4.6 | 94 |
| −5.0 | 7.8 | 100 |
| −7.5 | 9.2 | 100 |
| −10.0 | 14.0 | 100 |

The pain results were as follows:
  pain of 1=58%
  pain of 2=31%
  pain of 3=11%

A nearly linear relationship between level of vacuum and volume of blood collected was observed. The average volume of blood collected with vacuum applied prior and after piercing was approximately twice that collected with vacuum applied only after piercing without vacuum applied prior to piercing. See the results of Example 1 for this comparison (7.8 µL vs. 3.1 µL). The volume of blood collected was always above 1 µL for all levels of vacuum, except −2.5 psig.

Example 3

This example illustrates that localized heating of the area to be pierced followed by vacuum after piercing results in a greater volume of blood being extracted than does extraction with only vacuum after piercing.

Each of four people had his forearm (dorsal forearm, middle of forearm) punctured eight times (at eight different positions on the forearm) with a "BD ULTRA-FINE" lancet in a "MEDISENSE" lancet assembly with heat applied (45° C.) prior to piercing for two different time periods, 15 seconds and 60 seconds. A total of 32 runs were carried out, 16 runs where the pre-heating duration was 15 seconds and 16 runs where the pre-heating duration was 60 seconds.

Heat was applied with a heating block, which was an aluminum block having a square face covered with a "KAPTON" film heater element controlled by an "OMEGA" DP 41 temperature controller using a T-type thermocouple. Vacuum was applied after each puncturing for 30 seconds at −5.0 psig. Blood was collected into capillary tubes. The amount of blood collected was determined by measuring the length of blood in the tubes. The percentage of collections in which the volume of blood collected exceeded 1.0 µL was calculated. Pain was also tracked. Blood collection results are set forth in TABLE III.

TABLE III

| Pre-piercing heating duration (seconds) | Average volume of blood samples collected (µL) | Percent of samples having >1 µL of blood collected |
|---|---|---|
| 15 | 6.91 | 94 |
| 60 | 11.6 | 100 |

The pain results were as follows:
  pain of 1=91%
  pain of 2=9%
  pain of 3=0%

The average volume of blood collected using a pre-heating duration of 15 seconds was more than twice the average volume of blood collected at a post-puncturing vacuum level of −5.0 psig., with no pre-heating. See the results of Example 1 for this comparison (6.91 µL vs. 3.1 µL). The average volume of blood collected using a pre-heating duration of 60 seconds was approximately four times the average volume of blood collected at a post-puncturing vacuum level of −5.0 psig, with no pre-heating. See the results of Example 1 for this comparison (11.6 µL vs. 3.1 µL).

Example 4

This example illustrates the effect that stretching the skin upwardly with a vacuum has on the extraction of blood.

Each of four people had his forearm (dorsal forearm, middle of forearm) punctured eight times (at eight different positions on the forearm) with a "BD ULTRA-FINE" lancet in a "MEDISENSE" lancet assembly. Vacuum was applied for a period of 30 seconds prior to puncturing at −5.0 psig using two different vacuum fixtures. The first fixture was a 15 mm diameter vacuum fixture (i.e., a hollow cylindrical tube) used without a net strung across the opening of the tube. The second fixture was a 15 mm diameter vacuum fixture (i.e., a hollow cylindrical tube) used with a net strung across the opening of the tube. The net prevented skin from being raised up into the vacuum fixture. The same vacuum fixture used prior to puncturing was applied for a period of 30 seconds after puncturing. The fixture was held level with the plane of the skin. Four punctures were carried out per person per condition (without net, with net). Accordingly, it can be seen that a total of 32 runs were carried out. Blood was collected into capillary tubes. The amount of blood collected was determined by measuring the length of blood in the tubes. The percentage of collections in which the volume of blood collected exceeded 1.0 µL was calculated. Sensation of pain was also recorded. Blood collection results are set forth in TABLE IV.

TABLE IV

| Net across nosepiece | Average volume of blood sample collected (µL) | Percent of samples having >1 µL of blood collected |
|---|---|---|
| No | 5.2 | 87 |
| Yes | 0.6 | 19 |

The pain results were as follows:
  pain of 1=94%
  pain of 2=6%
  pain of 3=0%

The magnitude of the difference in volume of blood collected and success rates (i.e., percent of samples having >1 µL of blood collected) between the condition of stretching the skin in combination with a vacuum and the condition of not stretching the skin in combination with a vacuum was unexpected. The pain scores were low. This example demonstrates that the combination of skin stretching and applied vacuum significantly increased the volume of blood extracted.

Example 5

This example illustrates the effect the area of the extraction site has on blood collected.

Each of four people had his forearm (dorsal forearm, middle of forearm) punctured at 32 different positions on the forearm with a "BD ULTRA-FINE" lancet in a modified "MEDISENSE" lancet assembly. The "MEDISENSE" lancet assembly had been modified with a more powerful spring and a port had been added.

Vacuum was applied for less than five seconds prior to puncturing. The forearm was punctured under a vacuum of either −5.0 psig or −7.5 psig. The vacuum applied was maintained for 30 seconds after puncturing. The diameter of the pipette tip used to apply vacuum after puncturing was varied, with diameter of 4, 6, 8, and 10 mm being used. Four punctures per condition (diameter, vacuum level) were carried out per person. Accordingly, it can be seen that a total of 128 runs were carried out. Blood was collected into capillary tubes. The amount of blood collected was determined by measuring the length of blood in the tubes. The percentage of collections in which the volume of blood collected exceeded 1.0 μL was calculated. Sensation of pain was also recorded. Blood collection results are set forth in TABLE VA and VB.

TABLE VA vacuum level = −5.0 psig

| Vacuum diameter (mm) | Average volume of blood sample collected (μL) | Percent of samples having >1 μL of blood collected |
|---|---|---|
| 4 | 0.3 | 0 |
| 6 | 1.7 | 69 |
| 8 | 3.4 | 94 |
| 10 | 4.1 | 100 |

TABLE VB vacuum level = −7.5 psig

| Vacuum diameter (mm) | Average volume of blood sample collected (μL) | Percent of samples having >1 μL of blood collected |
|---|---|---|
| 4 | 0.8 | 25 |
| 6 | 3.1 | 94 |
| 8 | 3.4 | 81 |
| 10 | 6.3 | 94 |

The pain results were as follows:
 pain of 1=89%
 pain of 2=10%
 pain of 3=1%

The volume of blood collected and success rates (i.e., percent of samples having >1 μL of blood collected) were found to vary directly with the area of skin raised up into the device by the vacuum. A much greater volume of skin was raised up into the larger diameter pipette tip than into the smaller diameter pipette tips.

Example 6

This example illustrates that a plastic multiple point lancet can be used with heat and vacuum to collect a useful amount of blood.

Each of four people had his forearm (dorsal forearm, middle of forearm) punctured sixteen times (at sixteen different positions on the forearm) with a Greer Derma PIK® System for allergy testing (Greer Laboratories, Inc., Lenoir, N.C. 28645) modified to fit into a "MEDISENSE" lancet assembly. Pre-heating was carried out at approximately 40° C. and 45° C. for 15 and 60 seconds prior to puncturing prior to puncturing. Four punctures were carried out per condition (temperature, time) per person. Accordingly, it can be seen that a total of 64 runs were carried out.

Heat was applied with a heating block, which comprised an aluminum block having one face covered with a "KAPTON" film heater element controlled by an "OMEGA" DP 41 temperature controller using a T-type thermocouple and the opposite face in contact with the larger base of a frustum of a cone made of copper. The larger base of the frustum had a diameter of 0.50 in. The height of the frustum was 0.50 in. The smaller base of the frustum had a diameter of 0.35 in. The smaller base had a cylindrical opening having a diameter of 0.125 in. The cylindrical opening had a common axis with the frustum. The cylindrical opening reduced the heating surface of the copper frustum. Vacuum (−5.0 psig) was applied for a period of 30 seconds after puncturing. The vacuum in contact with the skin was formed by a pipette tip having a diameter of 8 mm. The pipette tip was held level with the plane of the skin. Blood was collected into capillary tubes. The amount of blood collected was determined by measuring the length of blood in the tubes. The percentage of collections in which the volume of blood collected exceeded 1.0 μL was calculated. Sensation of pain was also recorded. Blood collection results are set forth in TABLE VI.

TABLE VI

| Temperature (° C.)/Time (seconds) | Average volume of blood sample collected (μL) | Percent of samples having >1 (μL) of blood collected |
|---|---|---|
| 40/15 | 2.4 | 31 |
| 40/60 | 2.6 | 50 |
| 45/15 | 2.3 | 56 |
| 45/60 | 5.2 | 81 |

The pain results were as follows:
 pain of 1=100%
 pain of 2=0%
 pain of 3=0%

This example demonstrates that a blood extraction process employing a multi-point plastic lancet, pre-piercing heating, skin stretching, and post-piercing vacuum can extract at least 1 μL of blood at least 5% of the time.

Example 7

A prototype of the lancing assembly of this invention was tested in vitro for kinematic performance, using a "BD ULTRA-FINE" brand lancet and a solenoid valve supplied by the Lee Co, Model No. LHDA0511111H. Design parameters of the prototype are listed below. The definitions of these parameters were previously set forth.

| | |
|---|---|
| A | =30.7 mm$^2$ (diameter = 6.25 mm) |
| M | =1.2 grams |
| S | =10 mm |
| $X_p$ | =n/a |
| $K_s$ | =19.5 N/m |
| $X_s$ | =8.7 mm |
| $C_v$ | =0.015 |
| $Dt_v$ | =0.7 msec |
| $V_c$ | =0.01 cc |
| $V_v$ | =5 cc |

-continued

| | |
|---|---|
| P_a | =14.7 psia (=0 psig) |
| P_v | =6.7 psia (=−8.0 psig) |
| T_a | =25° C. |
| Ff | =0.13 N–0.18 N |

This configuration resulted in good lancing results when tested on human subjects. The measured lancet speed at the end of the stroke was 2.7 m/sec.

Example 8

Glucose detectors in the form of multiple-layer elements comprising the following layers, from top to bottom, were prepared:
(1) meter-contactable layer
(2) detecting layer
(3) overcoat layer
(4) blood-transporting layer
(5) covering layer The arrangement of the layers is shown schematically in FIGS. 11A and 11B of copending application entitled METHOD AND APPARATUS FOR OBTAINING BLOOD FOR DIAGNOSTIC TESTS, Attorney's Docket No. 6005. US.P2, filed on evendate herewith, the entirety of which is incorporated herein by reference. However, the overcoat layer is substantially coplanar with the blood-transporting layer as shown in FIG. 18 of Attorney's Docket No. 6005. US.P2.

The multiple-layer element was placed in an apparatus similar to that shown in FIG. 2. A vacuum of −7.5 psig was applied. The apparatus was placed in contact with the forearm of a volunteer. The skin of the forearm was stretched and it raised up into the nosepiece, where it came near to or into contact with the covering layer of the multiple-layer element. After the vacuum had been applied for five seconds, the lancet was fired into the skin by means of a pneumatic lancet assembly of the type illustrated in FIGS. 11 and 12. The lancet passed through the openings in the meter-contactable layer and in the covering layer. The lancet was retracted and blood began to emerge from the forearm of the volunteer. The vacuum aided in the extraction of blood until the blood reached the blood-transporting layer. The blood was then transported along the blood-transporting layer until it reached the detecting layer of the multiple-layer element. When the blood reached the detecting layer of the multiple-layer element, an electrical current was generated. This current was used to determine when to release the vacuum.

Eight volunteers were tested as described in the previous paragraph. The time required for the multiple-layer element to fill after the lancing operation was recorded. The type of multiple-layer element used in this example had one opening in the meter-contactable layer, as described in Example 8 and shown in FIGS. 11A, 11B, 15, and 18 of Attorney's Docket No. 6005. US.P2. The multiple-layer element was considered to be filled when a current of 1.5 µA was generated. The vacuum was then released and the integrated current (i.e., charge) was recorded. The lancing procedure and data collection were repeated four times per volunteer. Blood filled the multiple-layer element in less than 40 seconds for 97% of the tests. The average time required to fill the multiple-layer element was 15.9 seconds.

Example 9

Glucose detectors in the form of multiple-layer elements comprising the following layers, from top to bottom, were prepared:
(1) meter-contactable layer
(2) detecting layer
(3) overcoat layer
(4) blood-transporting layer
(5) covering layer The arrangement of the layers is shown schematically in FIGS. 11A and 11B of copending application entitled METHOD AND APPARATUS FOR OBTAINING BLOOD FOR DIAGNOSTIC TESTS, Attorney's Docket No. 6005. US.P2, filed on evendate herewith, the entirety of which is incorporated herein by reference. However, the overcoat layer is substantially coplanar with the blood-transporting layer as shown in FIG. 18 of Attorney's Docket No. 6005. US.P2.

The multiple-layer element was placed in an apparatus similar to that shown in FIG. 2. A vacuum of −7.5 psig was applied. The apparatus was placed in contact with the forearm of a volunteer. The skin of the forearm was stretched and it raised up into the nosepiece, where it came near or into contact with the covering layer of the multiple-layer element. After the vacuum had been applied for five seconds, the lancet was fired into the skin by means of a pneumatic lancet assembly of the type illustrated in FIGS. 16 and 17.

The lancet passed through openings in the meter-contactable layer and the covering layer of the multiple-layer element. The lancet was retracted and blood began to emerge from the forearm of the volunteer. As quickly as possible, the multiple-layer element was slid approximately 2 mm in the direction away from the electrical contacts. This type of movement is more fully described in copending application entitled METHOD AND APPARATUS FOR OBTAINING BLOOD FOR DIAGNOSTIC TESTS, Attorney's Docket No. 6005. US.P4, filed on evendate herewith, the entirety of which is incorporated herein by reference. The vacuum aided in the extraction of blood until the blood reached the blood-transporting layer. The blood was then transported along the blood-transporting layer until it reached the detecting layer of the multiple-layer element. When the blood reached the detecting layer of the multiple-layer element, an electrical current was generated. This current was used to determine when to release the vacuum.

Nine non-diabetic volunteers were tested as described in the previous paragraph. Each volunteer was tested with two types of multiple-layer element. One type of multiple-layer element had two openings in the meter-contactable layer, as described in Example 9 and shown in FIG. 16A of Attorney's Docket No. 6005. US.P2. The other type of multiple-layer element had one opening in the meter-contactable layer, as described in Example 9 and shown in FIG. 16B of Attorney's Docket No. 6005. US.P2. The time required for the multiple-layer element to fill after the lancing operation was recorded. The multiple-layer element was considered to be filled when a current of 1.5 µA was generated. The vacuum was then released. The lancing procedure and data collection were repeated eight times per volunteer per element. Blood filled the multiple-layer element having one opening in the meter-contactable layer in less than 40 seconds for 95% of the tests. Blood filled the multiple-layer element having two openings in the meter-contactable layer in less than 40 seconds for 96% of the tests. The average time required to fill the multiple-layer element having two openings in the meter-contactable layer was 14 seconds. The average time required to fill the multiple-layer element having one opening in the meter-contactable layer was 11 seconds.

Example 10

Figure 20:
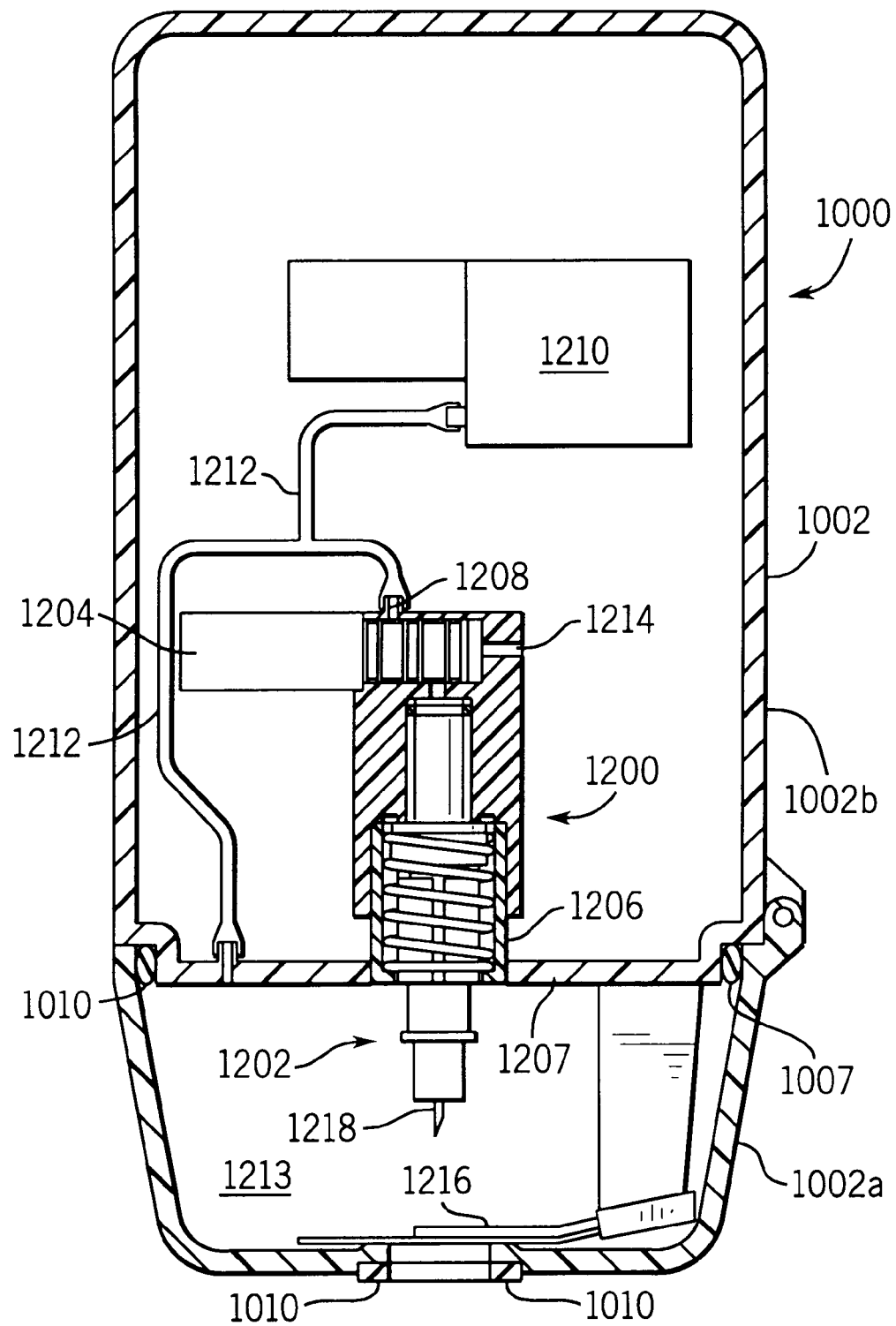
FIG. 20 is an elevational view, in cross section, of the lancing assembly of this invention installed in an embodiment of an apparatus of this invention.

FIG. 20 illustrates a preferred installation of the lancing assembly shown in FIGS. 11 and 12 inside a prototype of an embodiment of the blood collecting apparatus of this invention. Additional details of this embodiment can be found in copending application entitled METHOD AND APPARATUS FOR OBTAINING BLOOD FOR DIAGNOSTIC TESTS, Attorney's Docket No. 6005. US.P4, filed on even-date herewith, the entirety of which is incorporated herein by reference. The lancing assembly 1200, shown in its retracted pre-thrust position, has been fitted with a standard lancet assembly 1202 and a three-way solenoid valve 1204. The cap 1206 of the lancing assembly 1200 is fitted into the partition 1207 of the apparatus 1000, thereby forming an effective seal against the partition 1207. The apparatus 1000 comprises a housing 1002, which comprises a door portion 1002a and a body portion 1002b. The exit port 1208 of the lancing assembly 1200 is connected to a vacuum pump 1210 by means of a passageway 1212, such as, for example, a connecting tube. The passageway 1212 is also connected to a cavity 1213 inside the door portion 1002a of the apparatus 1000. In this manner, the vacuum pump 1210 can deliver an equal level of vacuum pressure to the cavity 1213 and to the exit port 1208. The vacuum pressure inside the cavity 1213 can be maintained at a level at which the apparatus 1000 operates, because the vacuum pump 1210 can draw evacuated air from the cavity 1213 at a rate faster than the rate at which ambient air leaks into the cavity 1213 by way of the door seal 1007, the seal placed against the skin of a patient 1010, and the seal formed between the cap 1206 and the partition 1207 (not shown). The body 1002b of the housing 1002 of the apparatus 1000 contains air having a pressure level equal to the ambient pressure surrounding the apparatus. The level of pressure inside the body 1002b of the housing 1002 does not change during operation of the apparatus because the body 1002b of the housing 1002 contains a sufficient number of openings (not shown) that communicate with the surrounding ambient air. The air inside the body 1002b of the housing 1002 can enter the lancing assembly 1200 through the inlet port 1214 when the solenoid valve 1204 is activated to begin the lancing step. The difference in air pressure between the ambient air inside the body 1002b of the housing 1002 and the evacuated air inside the cavity 1213 in the door portion 1002a of the housing 1002 brings about the differential gas pressure needed to operate the lancing assembly. During the lancing step, the thrusting motion of the lancet assembly 1202 is halted by a lancet stop 1216. The lancet stop 1216 has an opening (not shown) that allows the lancet 1218 to pass through and penetrate the skin which is placed against the seal 1010. The lancing assembly in FIG. 20 can thus be used in a manner substantially identical to that shown in FIGS. 15A, 15B, and 15C.

Various modifications and alterations of this invention will become apparent to those skilled in the art without departing from the scope and spirit of this invention, and it should be understood that this invention is not to be unduly limited to the illustrative embodiments set forth herein.

What is claimed is:

1. An assembly capable of providing an opening in an area of skin of a patient by means of lancet, comprising:
    (a) a holder for holding a lancet assembly;
    (b) a means for providing sufficient force to cause said holder to be maintained in a position whereby a lancet in said holder would be positioned away from said skin of said patient;
    (c) a means for allowing a gas to provide sufficient force to overcome the force provided by said holder maintaining means, whereby said gas causes said holder to be moved to a position whereby a lancet in said holder would be able to pierce said skin of said patient; and
    (d) a means for reducing level of pressure in said area of said skin of said patient below 0 psig.

2. The assembly of claim 1, further including a lancet assembly in said holder.

3. The assembly of claim 1, wherein movement of said holder is brought about by means of said gas acting on a piston attached to said holder.

4. The assembly of claim 3, wherein said holder maintaining means (b) is a piston biasing means.

5. The assembly of claim 4, wherein said piston biasing means is a spring.

6. An assembly capable of providing an opening in an area of skin of a patient by means of lancet, comprising:
    (a) a holder for holding a lancet assembly;
    (b) a means for providing sufficient force to cause said holder to be maintained in a position whereby a lancet in said holder would be positioned away from said skin of said patient; and
    (c) a means for allowing a gas to provide sufficient force to overcome the force provided by said holder maintaining means, whereby said gas causes said holder to be moved to a position whereby a lancet in said holder would be able to pierce said skin of said patient, wherein said holder maintaining means (b) is a piston biasing means, wherein said piston biasing means is a bellows.

7. The assembly of claim 1, wherein said means (c) comprises a piston attached to said holder, said piston being disposed in a bore, said bore being capable of being opened to allow sufficient gas at sufficient pressure to enter to move said piston, whereby said holder is moved to said position whereby a lancet in said holder would be able to pierce the skin of said patient.

8. An assembly capable of providing an opening in an area of skin of a patient by means of lancet, comprising:
    (a) a holder for holding a lancet assembly;
    (b) a means for providing sufficient force to cause said holder to be maintained in a position whereby a lancet in said holder would be positioned away from said skin of said patient; and
    (c) a means for allowing a gas to provide sufficient force to overcome the force provided by said holder maintaining means, whereby said gas causes said holder to be moved to a position whereby a lancet in said holder would be able to pierce said skin of said patient, wherein said means (c) comprises a piston attached to said holder, said piston being disposed in a bore, said bore being capable of being opened to allow sufficient gas at sufficient pressure to enter to move said piston, whereby said holder is moved to said position whereby a lancet in said holder would be able to pierce said skin of said patient, wherein said means (c) further comprises a valve having a first port, a second port, and a third port, said first port capable of communicating with a source of gas at a first pressure, said second port capable of communicating with said bore, said third port capable of communicating with a source of gas at a second pressure, said second pressure being lower than said first pressure.

9. The assembly of claim 7, further including a means for sealing said bore.

10. The assembly of claim 9, wherein said sealing means is an o-ring.

11. An assembly capable of providing an opening in an area of skin of a patient by means of lancet, comprising:
    (a) a holder for holding a lancet assembly;

(b) a means for providing sufficient force to cause said holder to be maintained in a position whereby a lancet in said holder would be positioned away from said skin of said patient; and (c) a means for allowing a gas to provide sufficient force to overcome the force provided by said holder maintaining means, whereby said gas causes said holder to be moved to a position whereby a lancet in said holder would be able to pierce said skin of said patient, wherein said means (c) comprises a piston attached to said holder, said piston being disposed in a bore, said bore being capable of being opened to allow sufficient gas at sufficient pressure to enter to move said piston, whereby said holder is moved to said position whereby a lancet in said holder would be able to pierce said skin of said patient, said assembly further including a means for sealing said bore, wherein said sealing means is a bellows.

12. An assembly capable of providing an opening in an area of skin of a patient by means of lancet, comprising:

(a) a holder for holding a lancet assembly;

(b) a means for providing sufficient force to cause said holder to be maintained in a position whereby a lancet in said holder would be positioned away from said skin of said patient; and (c) a means for allowing a gas to provide sufficient force to overcome the force provided by said holder maintaining means, whereby said gas causes said holder to be moved to a position whereby a lancet in said holder would be able to pierce said skin of said patient, wherein said means (c) comprises a piston attached to said holder, said piston being disposed in a bore, said bore being capable of being opened to allow sufficient gas at sufficient pressure to enter to move said piston, whereby said holder is moved to said position whereby a lancet in said holder would be able to pierce said skin of said patient, said assembly further including a means for sealing said bore, wherein said sealing means is a diaphragm.

13. The assembly of claim 1, further including a piston, attached to said holder, which piston (1) travels in a first direction in a bore when gas at a first pressure enters said bore and said first pressure exceeds the pressure of gas in said bore prior to said entry of said gas at said first pressure and (2) travels in a second direction in said bore when said holder maintaining means (b) overcomes the force of gas acting on said piston in said bore.

14. An assembly capable of holding a lancet assembly for providing an opening in skin of a patient, comprising:

(a) a housing having
 a bore having an axis;
 a valve fitted in a valve manifold;
 a first port in said valve manifold that allows said valve manifold to allow passage of gas at a first pressure through
 a first port in said valve;
 a second port in said valve manifold that allows said valve manifold to allow passage of said gas at said first pressure through a second port in said valve to enter said bore;
 a third port in said valve manifold that allows said valve manifold to allow passage of gas from said bore through a third port in said valve to a location having gas at a second pressure, said first pressure being greater than said second pressure;

(b) a piston disposed in said bore, said piston having a proximal end and a distal end, said proximal end adjacent to said second port and said distal end including a holder for holding a lancet, said piston capable of moving along the axis of said bore;

(c) means for biasing said piston so that said proximal end of said piston is in the furthest position away from the skin of said patient when said first port is closed.

15. The assembly of claim 14, wherein said piston biasing means (c) is a spring.

16. The assembly of claim 14, wherein said piston biasing means (c) is a bellows.

17. The assembly of claim 14, wherein said valve is actuated by a solenoid.

18. The assembly of claim 14, further including a means for sealing said bore.

19. The assembly of claim 18, wherein said means for sealing said bore is an o-ring.

20. The assembly of claim 18, wherein said means for sealing said bore is a bellows.

21. The assembly of claim 18, wherein said means for sealing said bore is a diaphragm.

22. A method for forming an opening in an area of skin of a patient in order to obtain blood, said method comprising the steps of:

(1) providing a lancing assembly capable of providing an opening in an area of skin of a patient by means of lancet, comprising:
  (a) a holder for holding a lancet assembly;
  (b) a means for providing sufficient force to cause said holder to be maintained in a position whereby a lancet in said holder would be positioned away from said skin of said patient;
  (c) a means for allowing a gas to provide sufficient force to overcome the force provided by said holder maintaining means, whereby said gas causes said holder to be moved to a position whereby a lancet in said holder would be able to pierce said skin of said patient;
  (d) a means for reducing level of pressure in said area of said skin of said patient below 0 psig; and
  (e) a lancing assembly in said holder, (2) positioning said lancing assembly sufficiently close to said skin of said patient so that a lancet in said lancet assembly can pierce said skin of said patient;

(3) reducing level of pressure in said area of said skin of said patient below 0 psig; and (4) causing said means (c) to allow a gas to provide sufficient force to overcome the force provided by said holder maintaining means, so that said holder is moved to a position whereby said lancet in said lancet assembly pierces said skin of said patient; and (5) causing said lancet to be retracted from said skin of said patient.

* * * * *